US009829602B2

(12) United States Patent
Bond et al.

(10) Patent No.: US 9,829,602 B2
(45) Date of Patent: Nov. 28, 2017

(54) METHOD AND SYSTEM FOR IDENTIFYING AND SAMPLING HYDROCARBONS

(71) Applicants: William E. Bond, Spring, TX (US); Robert J. Pottorf, Houston, TX (US)

(72) Inventors: William E. Bond, Spring, TX (US); Robert J. Pottorf, Houston, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 0 days.

(21) Appl. No.: 14/752,030

(22) Filed: Jun. 26, 2015

(65) Prior Publication Data
US 2016/0018558 A1 Jan. 21, 2016

Related U.S. Application Data

(60) Provisional application No. 62/026,449, filed on Jul. 18, 2014.

(51) Int. Cl.
*G01V 8/02* (2006.01)
*G01V 9/00* (2006.01)
*G01N 33/24* (2006.01)
*G01N 33/18* (2006.01)

(52) U.S. Cl.
CPC ............. *G01V 8/02* (2013.01); *G01V 9/007* (2013.01); *G01N 33/1833* (2013.01); *G01N 33/241* (2013.01)

(58) Field of Classification Search
CPC ...................................................... G01V 8/02
See application file for complete search history.

(56) References Cited

U.S. PATENT DOCUMENTS

| 7,704,746 | B1* | 4/2010 | White et al. ............. 436/56 |
|---|---|---|---|
| 8,312,768 | B2 | 11/2012 | Neira et al. |
| 8,492,153 | B2 | 7/2013 | Jones et al. |
| 8,599,382 | B2 | 12/2013 | Pierce, Jr. et al. |
| 8,883,417 | B2 | 11/2014 | Jacobs et al. |
| 2003/0170909 | A1 | 9/2003 | Schaumloffel |
| 2004/0037747 | A1 | 2/2004 | Sternberger et al. |
| 2007/0078610 | A1 | 4/2007 | Adams et al. |

(Continued)

FOREIGN PATENT DOCUMENTS

| EP | 0678758 | 10/1995 |
|---|---|---|
| EP | 2113796 | 11/2009 |

(Continued)

OTHER PUBLICATIONS

Abrams, M.A., et al., (2010), "Geochemical Evaluation of Ocean Surface Slick Methods to Ground Truth Satellite Seepage Anomalies for Seepage Detection", *AAPG Convention, Search and Discovery Article #40604*, pp. 1-18.

(Continued)

*Primary Examiner* — David Porta
*Assistant Examiner* — Hugh H Maupin
(74) *Attorney, Agent, or Firm* — ExxonMobil Upstream Research Company Law Department

(57) ABSTRACT

Method and system is described to exploration and development hydrocarbon resources. The method involves operations for exploring and developing hydrocarbons with one or more unmanned vehicles. The unmanned vehicles are used to obtain one or more samples that may be used to identify hydrocarbon systems, such as hydrocarbon seeps.

20 Claims, 7 Drawing Sheets

(56) References Cited

U.S. PATENT DOCUMENTS

| | | | |
|---|---|---|---|
| 2010/0042324 | A1 | 2/2010 | Murphy |
| 2010/0068821 | A1* | 3/2010 | St. Germain ................ 436/140 |
| 2011/0308790 | A1 | 12/2011 | Strapoc et al. |
| 2012/0105830 | A1* | 5/2012 | Pierce et al. .................... 356/72 |
| 2012/0165215 | A1 | 6/2012 | Andersen et al. |
| 2013/0037707 | A1 | 2/2013 | Lamberti et al. |
| 2013/0116126 | A1 | 5/2013 | Ashby et al. |
| 2014/0078865 | A1* | 3/2014 | Coste et al. ..................... 367/77 |
| 2014/0152455 | A1 | 6/2014 | Giori et al. |
| 2014/0191893 | A1* | 7/2014 | Fox et al. ........................ 342/27 |
| 2014/0284465 | A1* | 9/2014 | Pottorf et al. ................ 250/253 |
| 2014/0378319 | A1 | 12/2014 | Regberg et al. |
| 2015/0007648 | A1* | 1/2015 | Theron et al. ............. 73/152.23 |
| 2015/0038348 | A1 | 2/2015 | Ashby et al. |
| 2015/0177212 | A1* | 6/2015 | Thomas et al. ............... 114/331 |
| 2015/0224502 | A1 | 8/2015 | Pargett et al. |
| 2015/0268136 | A1* | 9/2015 | Detweiller ............... G01N 1/14 73/864.34 |

FOREIGN PATENT DOCUMENTS

| | | |
|---|---|---|
| EP | 2 273 251 | 1/2011 |
| EP | 2 584 355 | 4/2013 |
| GB | 2478511 | 9/2011 |
| KR | 20050045180 | 5/2005 |
| KR | 101313546 | 10/2013 |
| WO | 2004/025261 | 3/2004 |
| WO | 2007/008932 | 1/2007 |
| WO | WO 2013/071185 | 5/2013 |
| WO | 2013/148442 | 10/2013 |

OTHER PUBLICATIONS

ASTM International, (2011), "Standard Practices for Sampling of Waterborne Oils", pp. D4489-D4495.

Autonomous Surface Vehicles Limited, (2015), ASV Global, Retrieved Oct. 9, 2015, from C-Cat 5 Datasheet: http://www.asvglobal.com, pp. 1-4.

Caccia, M., et al., (2005), "Sampling Sea Surfaces with SESAMO", IEEE Robotics & Automation Magazine, pp. 95-105.

Chase, C.R., et al., (2010), "Real-Time Monitoring of Oil Using Ultraviolet Filter Fluorometry", Sea Technology, pp. 1-9.

Chelsea Technologies Group, Ltd., (2015), "UV AquaTracka Fluorometer", Retrieved Oct. 9, 2015 from http://www.chelsea.co.uk/allproduct/marine/fluorometers/uv-aquatracka-fluorometer, 2 pages.

CSafe Global (2015), AcuTemp AX56L, Retrieved Oct. 9, 2015 from http://www.acutemp/com/products-AcuTemp-AX56L, 1 page.

Dalgleish, F. R., et al., (2013), "Towards Persistent Real-Time Autonomous Surveillance and Mapping of Surface Hydrocarbons", OTC 24241, Houston: Offshore Technology Conference, pp. 1-18.

Engineering Toolbox, The, (2015) "The Engineering Toolbox—Liquids—Densities", Retrieved Oct. 9, 2015 from The Engineering Toolbox: http://www.engineeringtoolbox.com/liquids-densities-d_743.html, 8 pages.

National Oceanic and Atmospheric Administration, (2012), "Open Water Oil Identification Job Aid", Seattle: US Dept. of Commerce, pp. 1-52.

Caccia, M. et al., "Design and Exploitation of an Autonomous Surface Vessel for the Study of Sea-Air Interactions," Proceedings of the 2005 IEEE, Barcelona, Spain, pp. 3582-3587 (Apr. 2005).

Camilli, R. et al., "Integrating In-situ Chemical Sampling with AUV Control Systems," 2004 MTTS/IEEE Techno-Ocean Conf., Piscataway, NJ, pp. 101-109 (Nov. 9-12, 2004).

Chang, W.J. et al., "Evaluation of Boat Deployable Thin Film Oil Samplers," XP055216718, Offshore Technology Conf., Dallas, TX, 20 pgs. (1984).

Fries, D. et al., "Solar Robotic Material Sampler System for Chemical, Biological and Physical Ocean Observations," XP032075878, IEEE, 5 pgs. (Sep. 19, 2011).

Leighton, J., "System Design of an Unmanned Aerial Vehicle (UAV) for Marine Environmental Sensing," XP055217103, S.B., http://www.dtic.mil/docs/citations/ADA573151 , Massachusetts of Technology, 70 pgs. (Feb. 2013).

Robinson, B., "A Guide to the Sampling and Analysis of Waters, Wastewaters, Soils and Wastes," Environment Protection Authority, State Government of Victoria, 54 pgs. (Mar. 2000).

Aeschbach-Hertig, W., et al., (2000), "Palaeotemperature Reconstruction From Noble Gases in Ground Water Taking Into Account Equilibration With Entrapped Air", Nature, vol. 405, pp. 1040-1044.

Ballentine, C.J., et al., (2002), "Production, Release and Transport of Noble Gases in the Continental Crust", GeoScienceWorld, pp. 481-538.

Ballentine, C.J., et al., (1991), "Rare Gas Constraints on Hydrocarbon Accumulation, Crustal Degassing and Groundwater Flow in the Pannonian Basin", Earth and Planetary Science Letters, vol. 105, pp. 229-246.

Ballentine, C.J., et al., (1996), "A Magnus Opus: Helium, Neon, and Argon Isotopes in a North Sea Oilfield", Geochimica et Cosmochimica Acta., vol. 60, No. 5., pp. 831-849.

Ballentine, C.J., et al., (2002), "Tracing Fluid Origin, Transport and Interaction in the Crust", GeoScienceWorld, pp. 539-614.

Battani, A., et al., (2010), "Trinidad Mud Volcanoes: The Origin of the Gas", AAPG Memoir 93, pp. 225-238.

Bell, R.J., et al., (2007), "Calibration of an In Situ Membrane Inlet Mass Spectrometer for Measurements of Dissolved Gases and Volatile Organics in Seawater", Environ. Sci. Technol., vol. 41, pp. 8123-8128.

Bosch, A., et al., (1988), "Natural Gas Association With Water and Oil as Depicted by Atmospheric Noble Gases: Case Studies From the Southeastern Mediterranean Coastal Plain", Earth and Planetary Science Letters, vol. 87, pp. 338-346.

Camilli, R., et al., (2009), "Characterizing Spatial and Temporal Variability of Dissolved Gases in Aquatic Environments With In Situ Mass Spectrometry", Environ, Sci. Technol., vol. 43, pp. 5014-5021.

Camilli, R., et al., (2007), "Characterizing Marine Hydrocarbons With In-Situ Mass Spectrometry", MTS, 7 pages.

Camilli, R., et al., (2010), "Tracking Hydrocarbon Plume Transport and Biodegradation at Deepwater Horizon", Science, vol. 330, pp. 201-204.

Chung, H.M., et al., (1988), "Origin of Gaseous Hydrocarbons in Subsurface Environments: Theoretical Considerations of Carbon Isotope Distribution", Chemical Geology, vol. 71, pp. 97-103.

Crovetto, R., et al., (1982), "Solubilities of Inert Gases and Methane in H2O and in D2O in the Temperature Range of 300 to 600 K", J. Chem. Phys., vol. 78(2), pp. 1077-1086.

Dunn-Norman, S., et al., (2004), "Reliability of Pressure Signals in Offshore Pipeline Leak Detection", Dept. of the Interior, MMS TA&R Program, pp. 1-86.

Fomel, S., et al., (2007), "Poststack Velocity Analysis by Separation and Imaging of Seismic Diffractions", Geophysics, vol. 72(6), pp. U89-U94.

Heaton, T.H.E., et al., (1981), "Excess Air in Groundwater", J. Hydrol., vol. 50, pp. 201-216.

Hohl, D., et al., (2010), "Energy, Environment and Climate Directorate White Paper", DCO Energy, Environment and Climate Workshop, 38 pages.

Holbrook, W., et al., (2003), "Thermohaline Fine Structure in an Oceanographic Front From Seismic Reflection Profiling", Science, vol. 301, pp. 821-824.

Huc, A.Y., (2003), "Petroleum Geochemistry at the Dawn of the 21st Century", Oil & Gas Science and Technology, vol. 58(2), pp. 233-241.

IP.com, (2012), "Detection of Underwater Hydrocarbon and Related Fluid Seeps Using Reflection Seismic Data", 3 pages.

Jakuba, M.V., et al., (2011), "Toward Automatic Classification of Chemical Sensor Data From Autonomous Underwater Vehicles", IEEE/RSJ International Conference on Intelligent Robots and Systems, pp. 4722-4727.

Kharaka, Y.K., et al., (1988), "The Solubility of Noble Gases in Crude Oil at 25-100 C", Applied Geochemistry, vol. 3, pp. 137-144.

(56) References Cited

OTHER PUBLICATIONS

Kinsey, J.C., et al., (2011), "Assessing the Deepwater Horizon Oil Spill With the Sentry Autonomous Underwater Vehicle", IEEE/RSJ International Conference on Intelligent Robots and Systems, pp. 261-267.

Lamontagne, R.A., et al., (2001), "Response of METS Sensor to Methane Concentrations Found on the Texas-Louisiana Shelf in the Gulf of Mexico", Navel Research Laboratory, 14 pages.

Larter, S.R., et al., (1995), "Reservoir Geochemistry: Methods, Applications and Opportunities", The Geochemistry of Reservoir, Geological Society Special Publication No. 86, pp. 5-32.

Liu, W., et al., (2007), "Ternary Geochemical-Tracing System in Natural Gas Accumulation", Science in China Series D: Earth Sciences, vol. 50(10), pp. 1494-1503.

Macdonald, I.R., et al., (2002), "Transfer of Hydrocarbons From Natural Seeps to the Water Column and Atmosphere", Geofluids, vol. 2, pp. 95-107.

Makris, N.C., (2006), "Fish Population and Behavior Revealed by Instantaneous Continental Shelf-Scale Imaging", Science, vol. 311, pp. 660-663.

Mangelsdorf, K., et al., (2011), "Microbial Lipid Markers Within and Adjacent to Challenger Mound in the Belgica Carbonate Mound Province, Porcupine Basin, Offshore Ireland (IODP Expedition 307)", Marine Geology, vol. 282, pp. 91-101.

Narr, W., et al., (1984), "Origin of Reservoir Fractures in Little Knife Field, North Dakota", The American Association of Petroleum Geologists Bulletin, vol. 68(9), pp. 1087-1100.

Ozgul, E., (2002), "Geochemical Assessment of Gaseous Hydrocarbons: Mixing of Bacterial and Thermogenic Methane in the Deep Subsurface Petroleum System, Gulf of Mexico Continental Slope", Texas A&M University, Thesis, pp. 1-167.

Pinti, D.L., et al., (1995), "Noble Gases in Crude Oils From the Paris Basin, France: Implications for the Origin of Fluids and Constraints on Oil-Water-Gas Interactions", Geochimica et Cosmochimica Acta, vol. 59(16), pp. 3389-3404.

Prinzhofer, A., et al., (2003), "Gas Isotopes Tracing: An Important Tool for Hydrocarbons Exploration", Oil & Gas Science and Technology, vol. 58(2), pp. 299-311.

Ruddick, B., et al., (2009), "Waer Column Seismic Images as Maps of Temperature Gradient", Oceanography, vol. 22(1), pp. 192-205.

Sackett, W.M., (1977), "Use of Hydrocarbon Sniffing in Offshore Exploration", Journal of Geochemical Exploration, vol. 7, pp. 243-254.

Smith, S.P., et al., (1985), "Noble Gas Solubility in Water at High Temperature", GCA, vol. 46, p. 397.

Valentine, D,L., et al., (2010), "Asphalt Volcanoes as a Potential Source of Methane to Late Pleistocene Coastal Waters", Nature Geoscience, vol. 3, pp. 345-348.

Zaikowski, A., et al., (2010), "Noble Gas and Methane Partitioning From Ground Water: An Aid to Natural Gas Exploration and Reservoir Evaluation", Geology, vol. 18, pp. 72-74.

Zartman, R.E., et al., (1961), "Helium, Argon, and Carbon in Some Natural Gases", Journal of Geophysical Research, vol. 66, No. 1, pp. 277-306.

Zhang, Y., et al., (2011), "A Peak-Capture Algorithm Used on an Autonomous Underwater Vehicle in the 2010 Gulf of Mexico Oil Spill Response Scientific Survey", Journal of Field Robotics, vol. 26(4), pp. 484-496.

\* cited by examiner

METHOD AND SYSTEM FOR IDENTIFYING AND SAMPLING HYDROCARBONS

CROSS-REFERENCE TO RELATED APPLICATION

This application claims the benefit of U.S. Provisional Patent Application 62/026,449 filed Jul. 18, 2014 entitled METHOD AND SYSTEM FOR IDENTIFYING AND SAMPLING HYDROCARBONS, the entirety of which is incorporated by reference herein.

FIELD OF THE INVENTION

This invention relates generally to the field of hydrocarbon exploration and development. Specifically, the invention relates to operations for exploring and developing hydrocarbons (e.g., oil and/or gas) with one or more remote vehicles.

BACKGROUND

Hydrocarbon reserves are becoming increasingly difficult to locate and access, as the demand for energy grows globally. As a result, various technologies are utilized to collect measurement data and then to model the location of potential hydrocarbon accumulations. The modeling may include factors, such as (1) the generation and expulsion of liquid and/or gaseous hydrocarbons from a source rock, (2) migration of hydrocarbons to an accumulation in a reservoir rock, (3) a trap and a seal to prevent significant leakage of hydrocarbons from the reservoir. The collection of data may be beneficial in modeling potential locations for subsurface hydrocarbon accumulations.

Typically, reflection seismic is the dominant technology for the identification of hydrocarbon accumulations. This technique has been successful in identifying structures that may host hydrocarbon accumulations, and may also be utilized to image the hydrocarbon fluids within subsurface accumulations as direct hydrocarbon indicators (DHIs). However, this technology may lack the required fidelity to provide accurate assessments of the presence and volume of subsurface hydrocarbon accumulations due to poor imaging of the subsurface, particularly with increasing depth where acoustic impedance contrasts that cause DHIs are greatly diminished or absent. Additionally, it is difficult to differentiate the presence and types of hydrocarbons from other fluids in the subsurface by such remote measurements.

Current geophysical, non-seismic hydrocarbon detection technologies, such as potential field methods like gravity or magnetics or the like, provide coarse geologic subsurface controls by sensing different physical properties of rocks, but lack the fidelity to identify hydrocarbon accumulations. These tools may provide guidance on where in a basin seismic surveys should be conducted, but do not significantly improve the ability to confirm the presence of hydrocarbon seeps or subsurface hydrocarbon accumulations. Further, other technologies may include a remote vehicle to use optical sensing of an oil slick. See, e.g., Dalgleish, F. R. et al., Towards Persistent Real-Time Autonomous Surveillance and Mapping of Surface Hydrocarbons. OTC 24241, Houston: Offshore Technology Conference (2013). However, as such techniques do not obtain a sample, these techniques do not significantly enhance the ability to confirm the presence of hydrocarbon seeps or subsurface hydrocarbon accumulations.

Yet another technique may include monitoring hydrocarbon seep locations as an indicator of subsurface hydrocarbon accumulations. See, e.g., ASTM International, Standard Practices for Sampling of Waterborne Oils. D4489-95 (Re-approved 2011). However, these techniques are limited as well. These techniques may include remote monitoring to identify possible waterborne oil (e.g., oil slick) locations. This may be performed with satellite or airborne imaging of sea surface slicks. Then, a marine vessel can be deployed with a manned crew to determine the location of the slick and to obtain samples. However, the deployment of a marine vessel may be time consuming and expensive to deploy to the various locations. Further, the deployment may not be able to locate the oil slick. That is, the oil slick may have dissipated or moved to a different location as a result of changes in conditions, such as currents and/or wind. As such, conventional techniques are problematic and costly.

As a result, an enhancement to exploration and development techniques is needed. In particular, the exploration techniques used to locate potential seafloor seeps of hydrocarbons in a more accurate and cost-effective manner over conventional techniques are desired. These techniques may efficiently obtain samples from waterborne liquid hydrocarbons for indicators of a working hydrocarbon system in exploration areas, which may then be used to enhance basin assessment and to high-grade areas for further exploration.

SUMMARY

In one or more embodiments, a method for identifying hydrocarbons is described. The method may include obtaining a potential location of waterborne liquid hydrocarbons in a body of water using remote sensing data; directing an unmanned vehicle (e.g., UAV or USV) to the potential location; and obtaining a sample of the waterborne liquid hydrocarbons with the unmanned vehicle. The method may include performing remote sensing (e.g., synthetic aperture radar (SAR)) in a survey area to identify the potential location of waterborne liquid hydrocarbons.

Further, in one or more embodiments, a method for identifying hydrocarbons is described. The method includes transporting one or more sample containers on an unmanned vehicle to a potential location of waterborne liquid hydrocarbons in a body of water; contacting sampling material from one of the one or more sample containers with the waterborne liquid hydrocarbons; retrieving the sampling material having adhered waterborne liquid hydrocarbons as an obtained sample into one of the one or more sample containers on the unmanned vehicle; and storing the obtained sample in the sample container.

A hydrocarbon identification system is described. The hydrocarbon identification system may include an unmanned vehicle having a propulsion component, a communication component and a sample measurement component. The propulsion component may be configured to maneuver the unmanned vehicle, while the sample measurement component may be configured to obtain one or more samples for the waterborne liquid hydrocarbons and the communication component is configured to communicate signals associated with the obtained samples. The unmanned vehicle may be configured to be controlled via remote control communications or to be autonomously operated. Also, the unmanned vehicle may have a heating and cooling component configured to maintain the temperature within each of the sampling containers within a specified range; a control unit configured to communicate with the propulsion component to perform a large pattern search to detect hydrocarbons in an automated manner; and a hydrocarbon detection component configured to identify hydrocarbons.

In some of the embodiments, the method and system may include various enhancements. For example, the method may also include storing the sample comprises managing the temperature within the one of the one or more sample containers on the unmanned vehicle, wherein the temperature is maintained with the range between about −10° C. and about 10° C. Further, the method may include removing live microbes from the obtained samples prior to determining whether the obtained sample is associated with a hydrocarbon system.

Further, in some other embodiments, the method or system may include another unmanned vehicle. For example, the method may include transporting one or more sample containers (e.g., container having sampling material) on a deployment unmanned vehicle (e.g., UAV or USV) to a potential location of waterborne liquid hydrocarbons in a body of water; contacting sampling material from one of the one or more sample containers with the waterborne liquid hydrocarbons; retrieving the sampling material having adhered waterborne liquid hydrocarbons as an obtained sample into one of the one or more sample containers on the unmanned vehicle; and storing the obtained sample in the sample container on the unmanned vehicle. The sample container may be configured to: seal the sampling material within the sample container if hydrocarbons are not detected; unseal the sample container to provide interaction between the sampling material and the waterborne liquid hydrocarbons in a body of water when hydrocarbons are detected.

Moreover, in some embodiments, deployment unmanned vehicle and retrieval unmanned vehicle may be used. The deployment unmanned vehicle may have a deployment propulsion component, a deployment communication component, a sample deployment component and a deployment measurement component, wherein the deployment propulsion component is configured to maneuver the deployment unmanned vehicle, the deployment measurement component is configured to identify waterborne liquid hydrocarbons, the sample deployment component is configured to deploy a sample container into the identified waterborne liquid hydrocarbons, and the deployment communication component is configured to communicate signals associated with the operation of the deployment unmanned vehicle. The retrieval unmanned vehicle may include similar components along with a sample measurement component that is configured to retrieve the sample container.

Further still, in one or more embodiment, satellite-acquired, near-real time synthetic aperture radar (SAR) is used to guide one or more unmanned surface vehicles (USVs) to collect samples of waterborne oil emanating from natural hydrocarbon seeps for further analysis. The further analysis may be performed on the USV and/or at an onshore laboratory. The lab analyses of the collected samples may include gas chromatography and mass spectrometry analyses. The USV may be configured for deployments for extended periods of time. For example, the deployment may be for a time period of three-months or more. The speed that the USV may move may include speeds greater than 3.5 knots (kn). The USV may be configured to collect different numbers of samples. For example, the USV may be configured to collect 50 to 100 individual samples of waterborne oil during its deployment.

BRIEF DESCRIPTION OF THE DRAWINGS

The foregoing and other advantages of the present disclosure may become apparent upon reviewing the following detailed description and drawings of non-limiting examples of embodiments.

DETAILED DESCRIPTION

Figure 1:
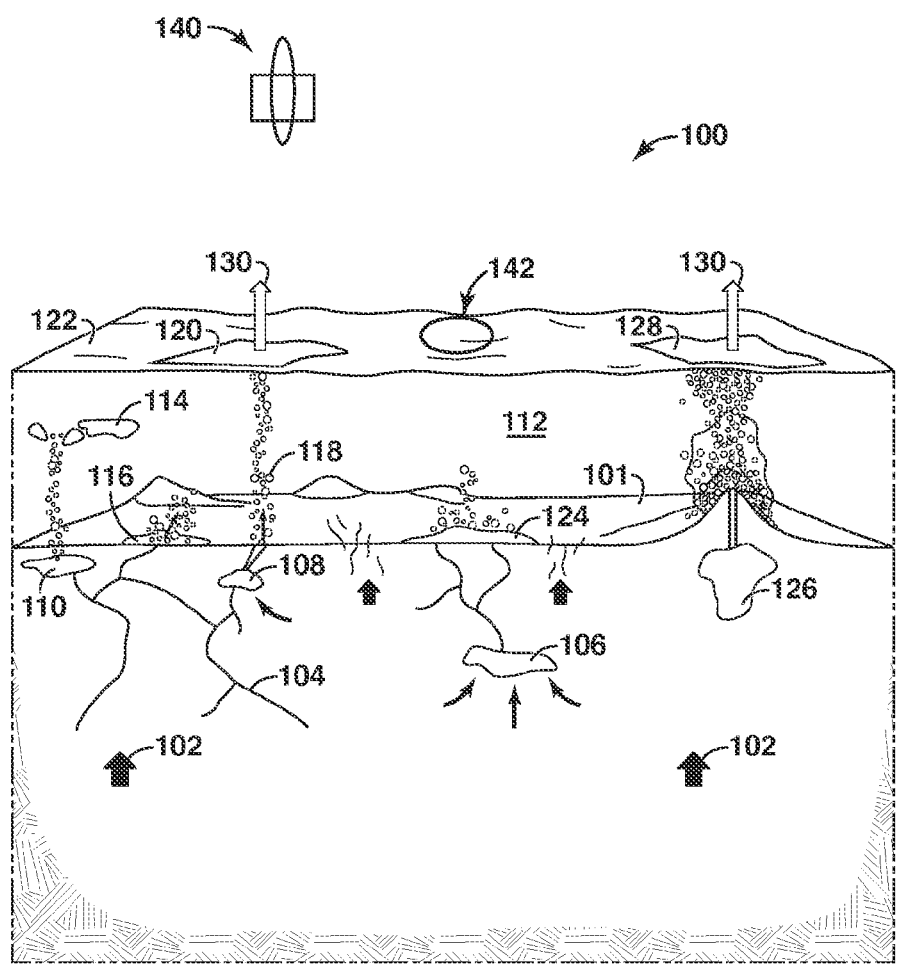
FIG. 1 is a side elevational view of a seafloor, body of water and air above the body of water.

In the following detailed description section, the specific embodiments of the present disclosure are described in connection with preferred embodiments. However, to the extent that the following description is specific to a particular embodiment or a particular use of the present disclosure, this is intended to be for exemplary purposes only and simply provides a description of the exemplary embodiments. Accordingly, the disclosure is not limited to the specific embodiments described below, but rather, it includes all alternatives, modifications, and equivalents falling within the true spirit and scope of the appended claims.

Various terms as used herein are defined below. To the extent a term used in a claim is not defined below, it should be given the broadest definition persons in the pertinent art have given that term as reflected in at least one printed publication or issued patent.

To begin, a seep is a natural surface leak of hydrocarbons (e.g., gas and/or oil). The hydrocarbon (e.g., petroleum) reaches the surface of the Earth's crust along fractures, faults, unconformities, or bedding planes, or is exposed by surface erosion into porous rock. The presence of a hydrocarbon seep at the seafloor or sea surface indicates that three basic geological conditions critical to petroleum exploration have been fulfilled. First, organic-rich rocks have been deposited and preserved (i.e. source presence). Second, the source has been heated and matured (i.e., source maturity). Third, secondary migration has taken place (i.e., hydrocarbon migration from the source location). While a surface seep of thermogenic hydrocarbons does not ensure that material subsurface oil and gas accumulations exist, seeps provide a mechanism to de-risk elements of an exploration play. That is, the seep may be utilized to remove uncertainty from the modeling of the subsurface and exploration operations.

Knowledge of the characteristics of naturally seeping hydrocarbons in marine environments can enhance exploration for oil and gas fields. As natural hydrocarbon seeps may result in a thin layer of waterborne liquid hydrocarbons (e.g., oil slicks) forming on the surface of the body of water, these waterborne liquid hydrocarbons may be identified on the surface of a body of water. If samples from the waterborne liquid hydrocarbons are properly collected, stored, and transported to a laboratory, then the samples can be analyzed to determine characteristics of the seeping hydrocarbons. The problem is that naturally occurring waterborne liquid hydrocarbons are difficult to inexpensively locate and sample with current methods. The conventional practice of sampling a slick requires the use of a manned marine vessel on which personnel visually locate the oil slick and then use hydrophobic fabric or netting to manually collect a sample. See, e.g., American Standards and Testing Association's Standard Practice D4489. This sampling approach is expensive because it involves lengthy deployments to collect samples due to the episodic nature of seeps, expense of personnel to operate the marine vessel, numerous sources of false positives, and the difficulty in visually locating oil slicks. Additionally, unfavorable lighting, weather, or sea conditions can make visually locating a slick very unlikely. Further still, many of the exploration locations of interest are in frontier areas of the oceans or seas, which are long distances from major ports and marine vessels (e.g., vessels of opportunity). The remote nature of these exploration locations increases the cost of the required manned vessel operations.

In the present disclosure, an enhancement to hydrocarbon identification and exploration techniques involves an enhanced unmanned vessel that is used to collect samples. The unmanned vessel may concurrently perform remote sensing over a region to identify potential waterborne liquid hydrocarbon locations and collect samples from the waterborne liquid hydrocarbon with the unmanned vehicle (UV), such as an unmanned surface vehicle (USV) and/or unmanned airborne vehicle (UAV). The concurrent operations include obtaining and transmitting the remote sensing data or information derived from the remote sensing data to one or more unmanned vehicles, wherein one of the unmanned vehicles is deployed to the waterborne liquid hydrocarbon location for sampling operations. In the present techniques, the remote sensing data is acquired, interpreted and communicated in near real-time. The term, "near real-time", means that information is obtained, processed, and acted upon prior to UV deployment (e.g., one or two weeks prior to UV deployment) and/or during the UV deployment. The term includes time delay between the acquisition of the remote sensing data and the time at which such data can be acted upon. The transmitted waterborne liquid hydrocarbon location may be used to guide the UV to the location of the suspected waterborne liquid hydrocarbons for sampling.

Beneficially, such techniques provide enhancements over conventional approaches. For example, as waterborne liquid hydrocarbon information is typically not obtained for a regional scale and not appropriately evaluated or sampled in the context of integrated hydrocarbon systems, the ability to identify and characterize seeps and thermogenic hydrocarbons provides enhancements for evaluating and capturing hydrocarbon reserves. The present techniques provide a method to locate seafloor hydrocarbon seeps accurately and cost-effectively over the play to basin scale (e.g., 1,000's to 100,000's square kilometers ($km^2$)) as a means to enhance basin assessment and to high-grade areas for exploration. This method overcomes conventional failures in frontier hydrocarbon exploration, which are associated with the inability to fully evaluate, understand, and appropriately risk the hydrocarbon system components. Also, the present techniques combined remote sensing with UV sampling created a less expensive means of identifying and evaluating waterborne liquid hydrocarbons.

In one or more embodiments, the method utilizes a combination of satellite and/or airborne remote sensing techniques along with an unmanned vehicle to characterize and map hydrocarbons in a marine environment in concurrent operations. The combination of remote sensing techniques along with unmanned vehicle that obtains samples provides a more complete characterization and mapping of hydrocarbons in the marine environment over play to basin scale exploration areas.

The remote sensing (e.g., satellite and/or airborne) may include synthetic aperture radar (SAR) along with other techniques. Remote sensing involves obtaining measurements from a distance of over 1000 feet from the body of water. As an example, remote sensing refers to the use of sensors mounted on satellites orbiting the earth to acquire synthetic aperture radar (SAR) images and/or other types of data that indicate the presence of naturally occurring waterborne liquid hydrocarbons. The remote sensing data may be integrated with other data to further enhance the process. For example, the remote sensing data may be combined with marine measurement data, which may be provided from a marine vessel (e.g., vessels performing other duties such as seismic and acoustic imaging, multibeam echosounder, side-scan sonar, sub-bottom profiler; magnetic and gravity surveying).

The sampling is performed by an unmanned vehicle (UV), such as an unmanned surface vehicle (USV) or unmanned airborne vehicle (UAV). The UV may include autonomous control or be remotely operated. The UV may include one or more modules configured to sample waterborne liquid hydrocarbons and/or to detect chemical or physical anomalies that are indicative of hydrocarbon seeps. For example, the UV may include a detection module, sampling module, propulsion module and communication module.

Beneficially, the present techniques provide a pre-drill technology that may determine the presence and location of thermogenic hydrocarbon seepages from the seafloor. Further, this method may be utilized to locate seafloor hydrocarbon seeps from slicks in a cost-effective manner over conventional approaches. As a result, this process provides geoscientists with an enhanced identification and/or verification technique for hydrocarbon systems. Various aspects of the present techniques are described further in FIGS. 1 to 11.

FIG. 1 is a diagram 100 illustrating the numerous subsurface sources and migration pathways of hydrocarbons present at or escaping from seeps on the ocean floor 101 and the method of detecting the resulting waterborne liquid hydrocarbons via a remote sensing unit 140 and unmanned vehicle 142. Hydrocarbons 102 generated at source rock (not shown) migrate upward through faults and fractures 104. The migrating hydrocarbons may be trapped in reservoir rock and form a hydrocarbon accumulation, such as a gas 106, oil and gas 108, or a gas hydrate accumulation 110. Hydrocarbons seeping from the gas hydrate accumulation may dissolve into methane and higher hydrocarbons (e.g., ethane, propane) in the ocean 112 as shown at 114, or may remain as a gas hydrate on the ocean floor 101 as shown at 116. Alternatively, oil or gas from oil/gas reservoir 108 may seep into the ocean, as shown at 118, and form waterborne liquid hydrocarbons 120 on the ocean surface 122. A bacterial mat 124 may form at a gas seep location, leaking from gas reservoir 106, and may generate biogenic hydrocarbon gases while degrading thermogenic wet gas. Still another process of hydrocarbon seepage is via a mud volcano 126, which can form waterborne liquid hydrocarbons 128 on the ocean surface. Waterborne liquid hydrocarbons 120 and 128 or methane gas 130 (and e.g., ethane, propane, etc.) emitted therefrom are signs of hydrocarbon seepage that are, in turn, signs of possible subsurface hydrocarbon accumulation. The signatures measured from each of these seeps may be analyzed according to disclosed methodologies and techniques herein to discriminate between the different origins of hydrocarbons encountered at these seeps. In particular, methodologies and techniques disclosed herein may discriminate between hydrocarbons that have migrated directly to the surface without encountering a trap within which they can be accumulated (e.g., a first source) and hydrocarbons that have leaked from a subsurface accumulation (e.g., a second source). If the presence and volume of such a hydrocarbon accumulation can be identified, it is possible the hydrocarbons from such an accumulation can be extracted.

To enhance the exploration of hydrocarbons, the diagram 100 includes the remote sensing unit 140 and unmanned vehicle 142. In this diagram 100, the remote sensing unit 140 is a satellite that is collecting data regarding the ocean surface 122. The remote sensing unit 140 is utilized to process the acquired data and provide an indication of identified waterborne liquid hydrocarbons, such as waterborne liquid hydrocarbons 120 and 128. Then, the locations of these waterborne liquid hydrocarbons are communicated to the unmanned vehicle 142, which is an unmanned surface vehicle (USV) in this diagram 100. The unmanned vehicle 142 may then move to a location near each of the waterborne liquid hydrocarbons 120 and 128 to obtain samples of the hydrocarbons in the waterborne liquid hydrocarbons. These samples may be stored and then analyzed to determine if the waterborne liquid hydrocarbons are associated with hydrocarbons seeps.

As may be appreciated, natural seepage is often episodic, which makes the collection of a waterborne oil sample difficult. A satellite image may indicate the likely presence of waterborne liquid hydrocarbons, but at a later time period (e.g., hours later) the waterborne liquid hydrocarbons may have dissipated and be undetectable upon arrival. Sometimes an area over a few square kilometers may have fairly consistent seepage, but the precise locations of the seeping origins and their waterborne liquid hydrocarbons may vary due to the environmental conditions.

As a result, the waterborne liquid hydrocarbons identified by satellite may be sporadic and not have a continuous presence for any considerable length of time. The UV provides the ability to confirm the presence of waterborne liquid hydrocarbons at its location with some confidence. Without this ability, there is a high likelihood that a vast majority of the samples collected may contain no significant amount of hydrocarbons. As such, the UV may have to spend considerable amounts of time searching in potential seepage locations.

To assist the UV, remote sensing may be utilized, such as SAR technology. SAR images may be obtained for substantial amounts of the area of interest at different intervals. For example, the intervals may be two days, although the frequency of acquisition, resolution of images, and size and location of images may be adjusted for different applications. Once analyzed, commands are issued to the UV, as appropriate, based at least partially on the information obtained from the SAR images. The method associated with this is further described in FIG. 2.

Figure 2:
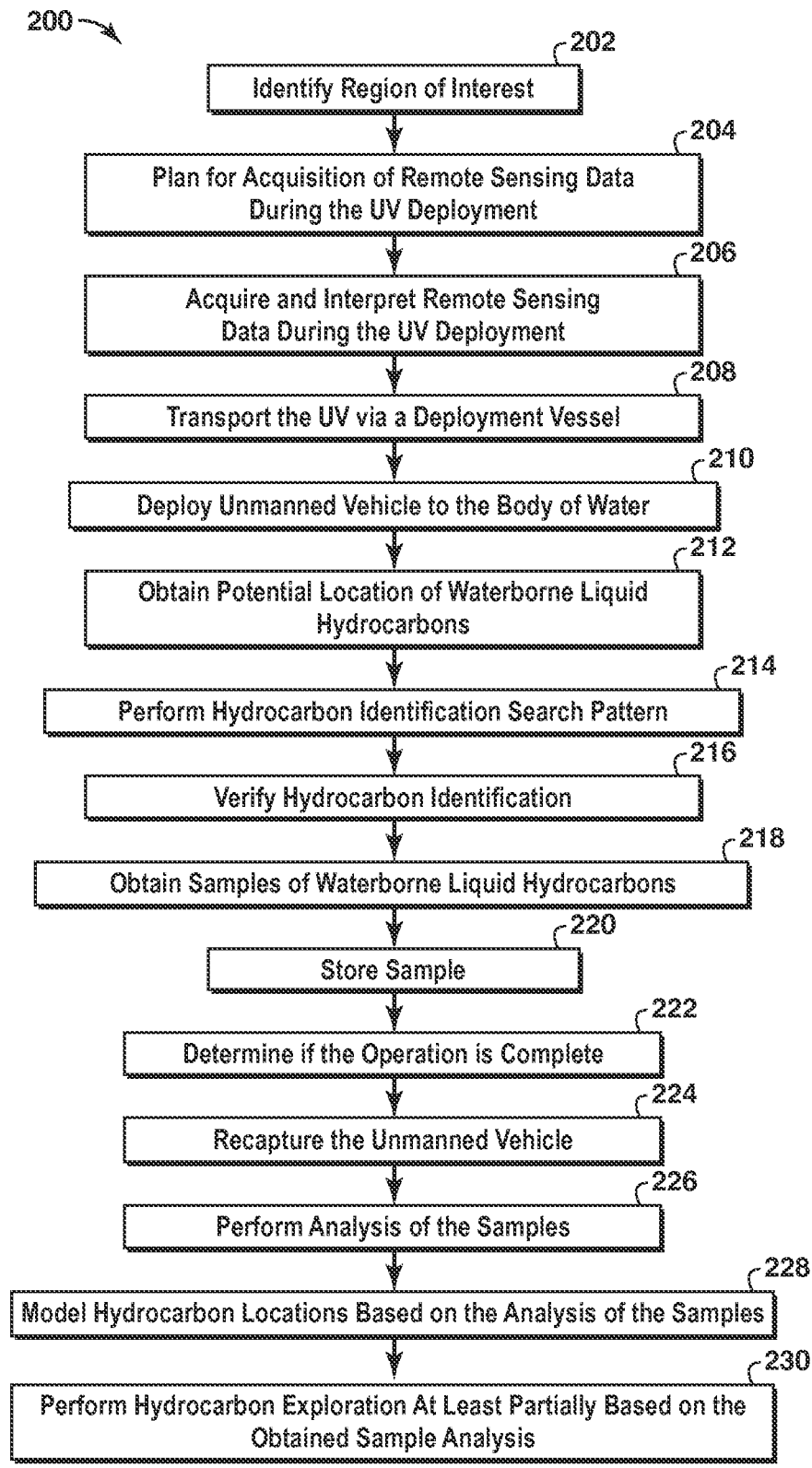
FIG. 2 is a flow chart for using remote sensing along with an unmanned vehicle to perform hydrocarbon exploration in accordance with an exemplary embodiment of the present techniques.

FIG. 2 is a flow chart 200 for using remote sensing along with an unmanned vehicle to perform hydrocarbon exploration in accordance with an exemplary embodiment of the present techniques. In this flow chart 200, various blocks relate to performing remote sensing for a region of interest, such as blocks 202 to 210, which may be referred to as a remote sensing stage. Other blocks involve searching for the waterborne liquid hydrocarbons in a searching stage, as shown in blocks 212 to 216, and sampling the waterborne liquid hydrocarbons, such as blocks 218 to 220, which may be referred to as a sampling stage. Finally, blocks 222 to 230 relate to other operations and the use of the sampled data for the hydrocarbon exploration.

The remote sensing stage is described in blocks 202 to 210. At block 202, a region of interest is identified. The identification of a region of interest may include performing various operations prior to deployment of the UV via remote sensing. The remote sensing survey may include satellite imagery and airborne surveys. The remote sensing techniques may include synthetic aperture radar (SAR) images and/or other types of data that indicate the presence of naturally occurring waterborne liquid hydrocarbons. For example, remote sensing data may be obtained and analyzed. This may involve reviewing available SAR data from an area of interest. This information may be used to identify areas of interest that have a higher probability of having seeps. Then, additional SAR or other data for the area of interest, such as wind direction and velocity for calculating potential movements of the surface hydrocarbons over time, may be analyzed to further refine and verify the locations that potentially include waterborne liquid hydrocarbons. At block 204, a plan for acquisition of remote sensing data during the UV deployment is developed. The UV deployment plan is developed after reviewing the obtained data. This may involve planning to acquire additional concurrent data for the area of interest, which is prior to UV deployment and continuing for the duration of the UV deployment. At block 206, acquire and interpret the remote sensing data during the UV deployment. The remote sensing data (e.g., SAR data) may be obtained prior to and/or concurrently with the UV deployment operations. At block 208, the UV may be transported by a deployment vessel. The deployment vessel may include a marine vessel or an airborne vessel that is capable of transporting the UV to a location in or near the body of water. Then, at block 210, the UV is deployed to the body of water. The deployment of the UV may include preparing the UV for operations and beginning the operations of the UV.

Once deployed, the searching for the waterborne liquid hydrocarbons in a searching stage is performed in blocks 212 to 216. The UV obtains a potential location for waterborne liquid hydrocarbons, as shown in block 212. The potential communication of the waterborne liquid hydrocarbons location may be directly to the unmanned vehicle and/or may be with a control unit that communicates with the unmanned vehicle. The control unit may be located on a marine vessel, airborne vessel or land-based location that communicates with the unmanned vehicle. Further, the communication of the location of the waterborne liquid hydrocarbons may include directional information, global positioning system coordinates and/or other suitable information to indicate the location of the waterborne liquid hydrocarbons on the ocean. At block 214, the unmanned vehicle performs a hydrocarbon identification search pattern for the potential waterborne liquid hydrocarbons. The search pattern may include moving the unmanned vehicle to the potential waterborne liquid hydrocarbons location, which may be one of various potential waterborne liquid hydrocarbons location identified from the remote sensing stage. Once at the location, a search pattern may be performed to locate the waterborne liquid hydrocarbons. As part of performing search, the UV may utilize one or more measurement components (e.g., hydrocarbon sensors) to locate the waterborne liquid hydrocarbons. For example, the sensors may include using a flourometer to identify the hydrocarbons, analyzing the water to detect certain wavelengths; and/or deploying a balloon above the UV to obtain and analyze infrared and visible light data to identify hydrocarbons; and/or deploying an unmanned aerial vehicle (UAV) with cameras or other sensors to identify hydrocarbons over a broad area. The use of the flourometer may include pumping surface compounds from the body of water (sea water and hydrocarbons) through a flourometer to identify hydrocarbons. The analysis of certain wavelengths may include receiving and analyzing signals from the surface of the body of water to detect certain wavelengths, which are utilized to identify hydrocarbons. The use of the balloon may include deploying a balloon above the unmanned vehicle, wherein the balloon has infrared and visible light detection components; obtaining infrared and visible light images for the region around the UV and analyzing the infrared and visible light images to identify hydrocarbons. The UAV may have active ultra-violet sensors that are configured to excite aromatic compounds in hydrocarbons and to detect resulting fluorescence emissions from the surface of the slick. The UAV may also have visible and infrared light cameras that can be used to investigate larger areas around the USV to locate slicks. Then, the UV may verify any identified hydrocarbons, as shown in block 216. The identification of hydrocarbons may be based on an indication from hydrocarbon sensors during the hydrocarbon identification search pattern, performing additional sensing operations and/or two or more indications from the hydrocarbon sensors. This verification may include performing a sequence of operations by the unmanned vehicle with two or more hydrocarbon sensors.

Once the searching stage has identified waterborne liquid hydrocarbons, the sampling stage may be performed in blocks 218 and 220. At block 218, the unmanned vehicle may obtain one or more samples of waterborne liquid hydrocarbons. As may be appreciated, the operation of the unmanned vehicle, which may be automated, may include various processes that repeat during the sample collection operations (e.g., period of time that the unmanned vehicle is obtaining samples). The unmanned vehicle may obtain samples at the potential waterborne liquid hydrocarbon location. For example, the unmanned vehicle may utilize the measurement components, such as one or more modules to obtain samples and a process control unit to manage the acquisition of the samples, calculate operational and sample parameters, determine adjustments to the operation of the unmanned vehicle and determine if additional samples should be obtained. Exemplary measurement components are described further below. Then, the samples may be stored in the UV, as shown in block 220. The storage of the samples may include storing the samples in individual compartments, which are isolated from each other to lessen any cross contamination. Exemplary techniques to store of the samples are described further below. At block 222, a determination is made whether the sample collection operations is complete. The determination may include obtaining a specific number of samples. Alternatively, as the samples may include different information, the determination may include analyzing one or more of the samples on the unmanned vehicle via respective measurement equipment to determine if additional samples should be obtained. If the sample collection operations are not complete, the process may continue with the UV obtaining another potential waterborne liquid hydrocarbon location, as shown in block 212.

However, if the operations are complete, the unmanned vehicle may be recaptured or redeployed to another potential waterborne liquid hydrocarbons location, as shown in block 224. The recapture and redeployment of the unmanned vehicle may include transmitting the location of the deployment vessel for retrieval or having the UV return to a specific location, which may be stored in memory on the unmanned vehicle.

Then, at block 226, the obtained samples may be analyzed. The analysis of the samples may include providing the samples to a laboratory to perform the analysis, performing the analysis on a marine vessel that deploys the unmanned vehicle, and/or obtaining results from the unmanned vehicle after it performs the analysis. The analysis (which may be in a laboratory or onboard a deployment vessel) using fluorometry, gas chromatography (GC), and/or other GC-MS (mass spectrometry)-MS or GC-GC time of flight mass spectrometry or additional techniques to obtain biomarkers and other indicators of hydrocarbon source facies and thermal maturity. In particular, this method may include determining the presence and estimating information, such as depth, type, quality, volume and location, about a subsurface hydrocarbon accumulation from the measured data from the samples acquired by the unmanned vehicle. The samples may be subjected to three independent analysis technologies, such as clumped isotope geochemistry, noble gas geochemistry, and microbiology. These may each be utilized to provide additional information about the depth, fluid type (oil vs. gas) and quality, and volume of subsurface hydrocarbon accumulations. That is, the method may integrate existing and new biological and geochemical indicators to provide insights in opportunity identification. In addition, the integration of these biological and geochemical indicators with geological/geophysical contextual knowledge with the other geological and measurement data further provides enhancements to hydrocarbon opportunity identification. These analysis techniques are described in Intl. Patent Application Pub. Nos. 2013119350; 2013148442; and 2013070304.

In one or more embodiments, the sampling operations may also lessen contamination by removing live microbes from the obtained samples. The removal of microbes may involve spraying the sample with a compound that kills the microbes as it is being retrieved or once the sample is within the compartment. This configuration may include a pump and nozzle disposed within each sampling container. Alternatively, sampling material may include a compound that kills living microbes captured by the sampling material.

In addition, with the obtained samples, the unmanned vehicle may also obtain other measurement data, such as camera images, temperature data, mass spectrometric data, conductivity data, fluorometric data, and/or polarization data, for example. The data can be in the format of images, raw data with specific format for the component, text files, and/or any combination of the different types. Other sensors may include functionality to provide chemical specificity of applied sensors (e.g., mass spectrometry). These sensors may discriminate thermogenic hydrocarbons, which may be preferred, from biogenic hydrocarbons and may determine whether the seep is associated with gas, oil, or a combination of gas and oil.

With the obtained samples, hydrocarbon locations may be modeled based on the analysis of the samples, as shown in block 228. The analysis of the samples may be integrated with other data to enhance or verify a subsurface model. As an example, the sample analysis data may be organized with the location of the unmanned vehicle or another location to correlate the sample analysis data with other measurements or models of the subsurface geology. That is, different types of data may be integrated based on location information associated with the respective data to enhance the exploration operations. For example, sample analysis data may be integrated with seismic, gravity, and magnetic data that have been combined to create subsurface models of the geology and hydrocarbon system in a region. The subsurface models are further enhanced by the results of microbial ecology, clumped isotopes, and noble gas signatures from samples acquired by the unmanned vehicle.

Finally, as shown in block 230, the hydrocarbon exploration is performed at least partially based on the obtained sample analysis. The hydrocarbon exploration may include analyzing the obtained sample to determine whether the waterborne liquid hydrocarbons are associated with a thermogenic or biogenic hydrocarbon system, obtaining additional measurement data associated with the waterborne liquid hydrocarbons, determining a location for hydrocarbons based at least partially on the waterborne liquid hydrocarbons, designating a drilling location for discovery of hydrocarbons based on the analysis of the sample. The determination of a location for hydrocarbons may include analyzing the sample analysis data to determine one or more of the hydrocarbon accumulation type, quality, depth and volume obtained from the microbial ecology, clumped isotope and noble gas signatures and/or these data integrated with the geological and geophysical data. The hydrocarbon exploration may include drilling a well to provide access to the hydrocarbon accumulation. Further, the exploration operations may also include installing a production facility configured to monitor and produce hydrocarbons from the production intervals that provide access to the subsurface formation. The production facility may include one or more units to process and manage the flow of production fluids, such as hydrocarbons and/or water, from the formation. To access the production intervals, the production facility may be coupled to a tree and various control valves via a control umbilical, production tubing for passing fluids from the tree to the production facility, control tubing for hydraulic or electrical devices, and a control cable for communicating with other devices within the wellbore.

Beneficially, the sample analysis data provides an enhancement in the exploration of hydrocarbons. In particular, the method may be utilized prior to drilling operations to reduce exploration risk by providing more information about the waterborne liquid hydrocarbons. As a result, this method provides a cost-effective technique to enhance basin assessment and/or to high-grade areas for hydrocarbon exploration. The sample analysis data may be integrated with seismic, gravity, magnetics, and acoustic data from surface surveys to provide an enhanced method to locate seafloor seeps of thermogenic hydrocarbons cost-effectively over large areas.

As yet another enhancement, the present techniques may involve the use of two or more unmanned vehicle. For example, one or more sample containers may be transported on a first or deployment unmanned vehicle (e.g., UAV or USV) to a potential location of waterborne liquid hydrocarbons in a body of water. The deployment unmanned vehicle may use the hydrocarbon identification techniques, noted above, to determine the location of the waterborne liquid hydrocarbons. Once identified, the deployment unmanned vehicle may drop, lower, launch or otherwise dispose one or more sample containers into the waterborne liquid hydrocarbons. Then, the sampling material may contact the waterborne liquid hydrocarbons. Then, the sampling material, which has adhered waterborne liquid hydrocarbons, is retrieved on a second or retrieval unmanned vehicle (e.g., UAV or USV). The retrieval unmanned vehicle may be used to store the obtained samples, which may involve the storing of the samples by managing the temperature (with the range between about $-10°$ C. and about $10°$ C.) within the sample containers on the retrieval unmanned vehicle. The sample containers may be retrieved via a hook and reel configuration, magnet or other suitable retrieval method.

In this configuration, the sample containers may include various configurations. For example, the sample containers may include sample material, as noted above, along with a spool or may include other configurations. For example, the sample container may be a canister that has the sampling material sealed within the canister's housing. The sample container may include sensor or active component that is utilized to detect the presence of hydrocarbons. For instance, the sample container may be configured to: seal the sampling material within the sample container if hydrocarbons are not detected; and unseal the sample container to provide interaction between the sampling material and the waterborne liquid hydrocarbons in a body of water when hydrocarbons are detected. Further, the sealing and unsealing operation may also be configured to be on a timer, remote activated and other such techniques. In particular, the sample container may be configured to seal the canister after a set period of time once the canister has been unsealed.

To locate the sample containers for retrieval, the sample containers and the retrieval unmanned vehicle may include locating components. That is, the sample containers may include a locating beacon (e.g., an audible notification or other such communication equipment) and the retrieval unmanned vehicle may be configured to detect and navigate to the locating beacon.

As an example, the deployment unmanned vehicle may have a deployment propulsion component, a deployment communication component, a sample deployment component and a deployment measurement component, wherein the deployment propulsion component is configured to maneuver the deployment unmanned vehicle, the deployment measurement component is configured to identify waterborne liquid hydrocarbons, the sample deployment component is configured to deploy a sample container into the identified waterborne liquid hydrocarbons, and the deployment communication component is configured to communicate signals associated with the operation of the deployment unmanned vehicle. To manage the temperature of the samples, the deployment unmanned vehicle may include a heating and cooling component configured to maintain the temperature within the sampling container within a specified range.

Further, mapping of waterborne liquid hydrocarbon locations may be useful for locating survey areas for acquisition of other survey data. The waterborne liquid hydrocarbons locations, which are determined to be associated with an active hydrocarbon system, may be useful to further assist collection or verification from other technologies. Accordingly, this integrated method may be utilized to further enhance the exploration activities.

Figure 3:
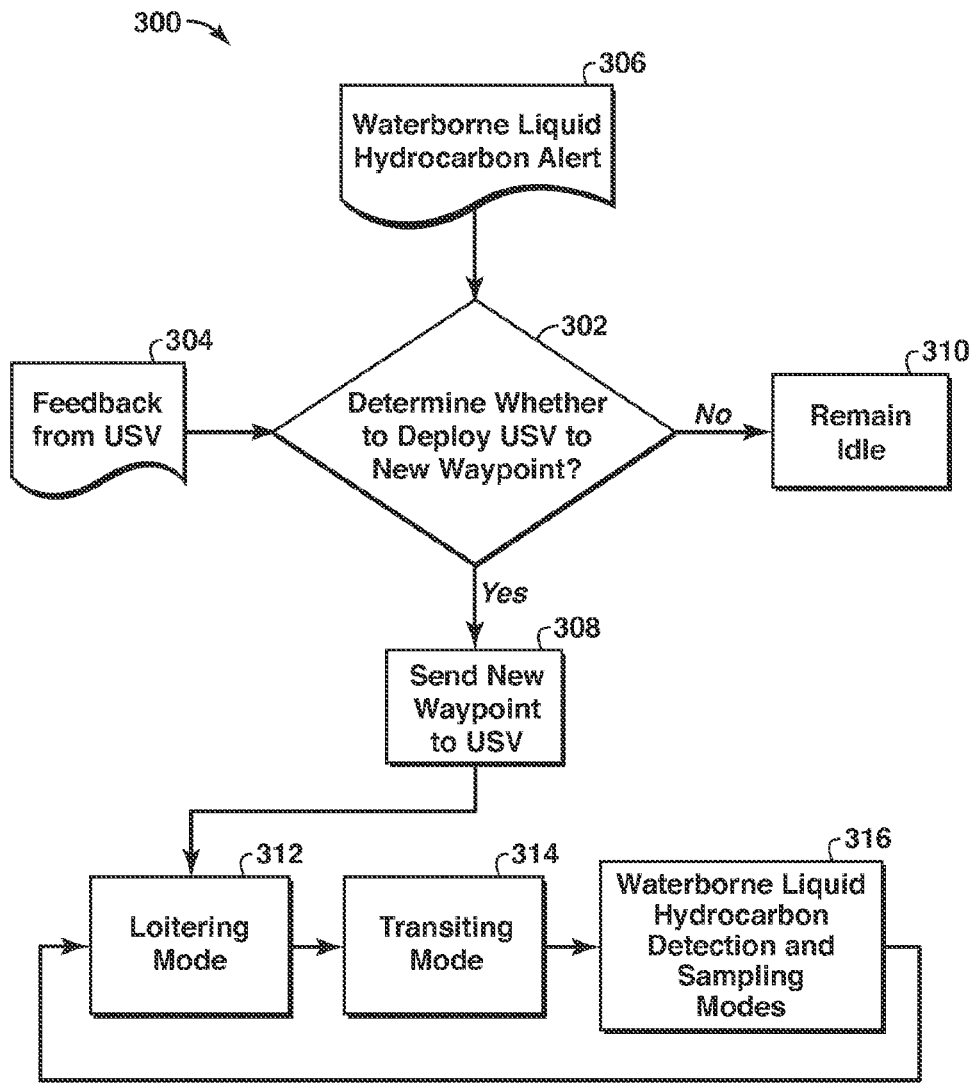
FIG. 3 is a diagram for using remote sensing with an unmanned surface vehicle to perform hydrocarbon identification in accordance with an exemplary embodiment of the present techniques.

FIG. 3 is a diagram 300 for using remote sensing with an unmanned surface vehicle to perform hydrocarbon identification in accordance with an exemplary embodiment of the present techniques. This example may also be used for a UAV, as well. In this diagram 300, a control unit on the deployment vessel or at a control center may communicate with the unmanned surface vehicle (USV) to perform the waterborne liquid hydrocarbon identification. The control unit functionality is shown in blocks 302 to 310, while the USV's functionality is shown in blocks 312 to 316.

For the control unit on the deployment vessel or at a control center, control logic, as shown in block 302, may be utilized to obtain information from various sources, such as USV feedback data in block 304 and waterborne liquid hydrocarbons alert data in block 306; and determine whether to send the USV to another waypoint, as shown in block 308, or maintain the USV in the current mode by remaining idle, as shown in block 310.

For the input data, the waterborne liquid hydrocarbons alert data may include satellite images that are acquired and analyzed concurrently with the USV deployment. If waterborne liquid hydrocarbons are detected, notifications or alerts regarding any potential waterborne liquid hydrocarbons may be communicated to the control unit or the USV. The location and/or outlines of the waterborne liquid hydrocarbons may be provided in the form of geo-referenced shape files. Then, the location and outlines may be analyzed to determine if the USV should be deployed to the location. The determination may include analysis of the waterborne liquid hydrocarbons outline in context with other data and previous waterborne liquid hydrocarbons indications, and a decision is made on whether or not to target the recently identified waterborne liquid hydrocarbons. The USV feedback data may include updates on the location and/or mode of operation for a specific USV.

After a decision is made to target a suspected waterborne liquid hydrocarbon location, a new or updated waypoint is relayed to the USV, as shown in block 308. The instruction to the USV to may include transmitting an updated waypoint, along with specific speed. The speed information may be useful because of the temporal variation of many seeps. The USV may initially be placed into a "loitering mode", as shown in block 312. The "loitering mode" may involve energy supply conservation operations. This may involve the USV remaining idle until another waterborne liquid hydrocarbon location is provided. Once a waterborne liquid hydrocarbon location is provided, the USV may enter into a "transiting mode", as shown in block 314. The "transiting mode" may involve the USV traveling to the waterborne liquid hydrocarbon location. The speed that the USV travels may be based on the speed information.

Once the USV arrives at the indicated location, the USV enters "waterborne liquid hydrocarbon detection mode", as shown in block 316. In "waterborne liquid hydrocarbon detection mode", the USV performs a spiral search pattern, increasing in radius away from the initial waypoint. The hydrocarbon search radius may be around 500 meter (m), with each subsequent radii increasing by about 500 m per rotation. After the USV reaches a radius of perhaps 2 kilometers (km), this pattern is ended or repeated, as appropriate. To detect the waterborne liquid hydrocarbons, the USV may use various sensors to identify the hydrocarbons. For example, the hydrocarbon detection sensors may involve using ultraviolet technology to view the water's surface from some distance above the surface to confirm the presence of waterborne liquid hydrocarbons. See, e.g., Chase et al., 2010. Alternatively, the sensors may include flow-through optical sensors that are used to confirm the presence of oil in the water. See, e.g., Dalgleish et al., 2013. As yet another, the USV may have active ultra-violet components that are configured to excite aromatic compounds in hydrocarbons and to detect resulting fluorescence emissions from the surface of the slick. The USV may also have visible and infrared light cameras that can be used to investigate larger areas around the USV to locate slicks.

Once the waterborne liquid hydrocarbons are verified, then the USV enters into "waterborne liquid hydrocarbon sampling mode". In this mode, the USV deploys one of its sampling devices and initiates a new trajectory, such as a sampling pattern. The sampling pattern may have a more narrow radius, as compared to the hydrocarbon search radius (about 10 m radius as compared to 500 m radius) and may be performed at a slower speed (e.g., approximately 1 m/s) spiral. This sampling pattern may be performed for a time period of about half an hour. The spiral increases in radius by about 5 m for every rotation. The spiral expands to perhaps a 75 m radius before ending. Upon conclusion, the sampling material is spooled back into the container, and the container is sealed shut. This sealing may isolate the sampling material from other samples that are obtained to lessen any contamination. Then, the USV may resume "waterborne liquid hydrocarbon detection mode" or may enter "loitering mode." As an example, after the USV collects a certain number of samples (e.g., two or more samples) from the waterborne liquid hydrocarbons, the UV may enter a "loitering mode" until further instructions are provided. This prevents oversampling of waterborne liquid hydrocarbons from a single location, which is not as efficient with the sampling material.

Figure 4:
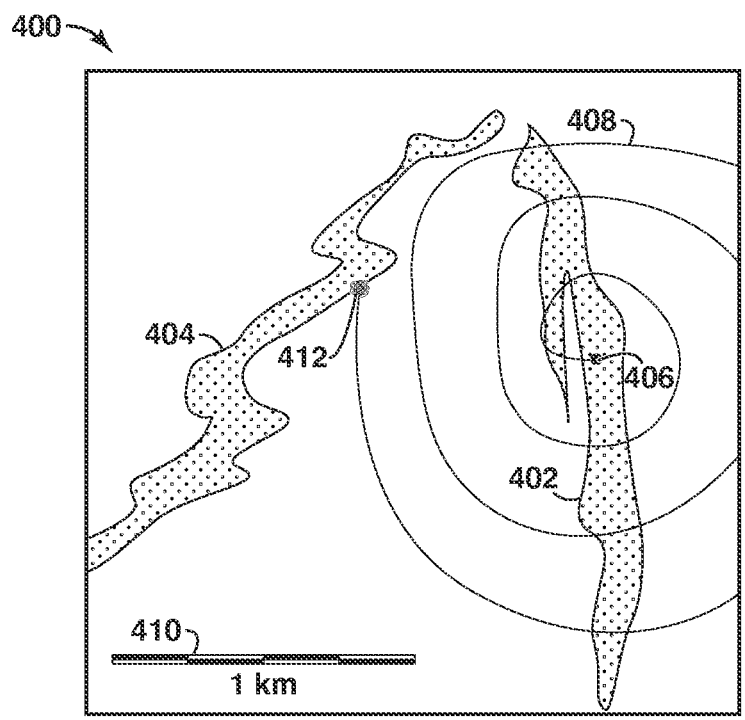
FIG. 4 is a diagram of an exemplary search pattern in accordance with an exemplary embodiment of the present techniques.

FIG. 4 is a diagram 400 of an exemplary search pattern in accordance with an exemplary embodiment of the present techniques. In this diagram 400, waterborne liquid hydrocarbons are identified from remote sensing data as an oil slick 402. Based on environmental conditions, the oil slick 402 may migrate to a different location, as shown by oil slick 404. Based on the remote sensing data, the USV may be directed to an initial waypoint 406 in a "transiting mode". At the initial waypoint 406, if the USV does not detect hydrocarbons, the USV may begin "waterborne liquid hydrocarbon detection mode". That is, the USV may perform a spiral search pattern 408, increasing in radius away from the initial waypoint 406. As noted above, the hydrocarbon search radius may be around 500 meter (m), with each subsequent radii increasing by about 500 m per rotation, which is indicated by the scale 410. This pattern 408 may continue until the USV detects hydrocarbons, as indicated by the waypoint 412. At this waypoint 412, the USV enters the "waterborne liquid hydrocarbon sampling mode". That is, the USV begins a different search pattern, as noted above, to collect the samples.

To collect samples, the UV (e.g., USV) may include various sampling containers. For example, obtaining of the samples may be performed with the UV having an assembly including 50 to 100 individual sampling containers. Each sample container includes sampling material that is deployed from the sample container onto the surface of the water and then retrieved back into the sample container. The hydrocarbons that contact the sampling material adhere to the material, and then the sampling device is retrieved back into the sampling container. The sampling material may be TFE-fluorocarbon polymer screening fabric and may have a thickness of about 0.1 millimeters (mm) to 0.7 mm, or more preferably about 0.3 mm. The sampling container may be sealed and temperature-controlled for the duration of the USV deployment.

Further, as another example, if two or more unmanned vehicle are used, one unmanned vehicle may be used to deploy the sample containers and another unmanned vehicle may be used to retrieve the sample containers. The deployment unmanned vehicle may perform different search patterns to locate the hydrocarbons, as noted above. Then, the other or retrieval unmanned vehicle may either use the search pattern to identify the sample containers or may use the locating techniques to obtain the sample containers.

Figure 5:
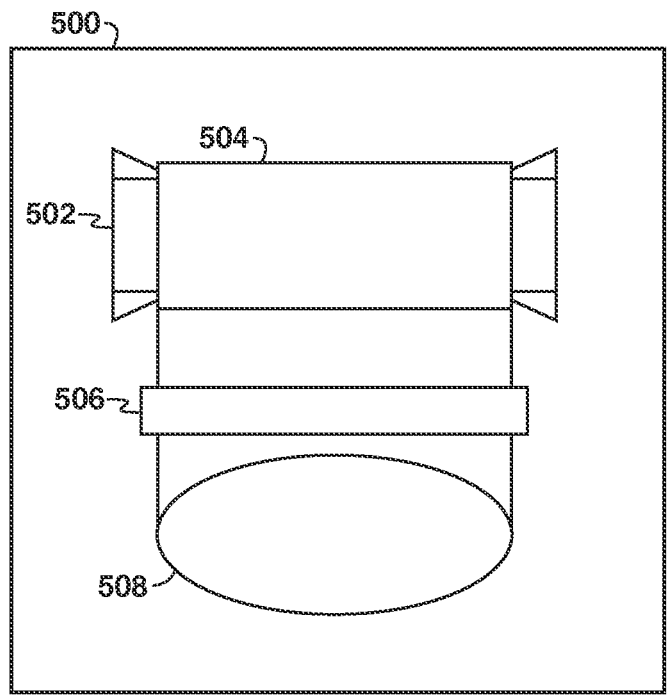
FIG. 5 is a diagram of an exemplary sample container in accordance with an exemplary embodiment of the present techniques.

FIG. 5 is a diagram of an exemplary sample container 500 in accordance with an exemplary embodiment of the present techniques. In this sample container 500, sampling material 504 may be disposed around a spool 502. The sampling material 504 may be attached to the spool 502 at one end, while the other end of the sampling material 504 may be attached to a buoyant weight 508. The buoyant weight 508 may be adapted to float on the body of water to maintain the sampling material 504 in contact with the surface of the body of water. To control the distribution of sampling material 504, a guide member 506 may be disposed between the spool 502 and the buoyant weight 508. The spool 502 may dispense and retrieve the sampling material 504 through the use of a motor and/or other mechanism (not shown). Beneficially, by having the sampling material 504 in an individual sample container, cross contamination from different samples may be lessened.

As an example, the sampling material 504 may be deployed on a spool 502 that is about 12 centimeters (cm) wide. If the configuration includes 50 to 100 individual sampling containers, each of the individual sampling containers contains one such spool 502. The spool 502 is actuated to activate the deployment and retrieval of the sampling strip of the sampling material 504. The end of the strip is weighted, such as the buoyant weight 508, so that tension exists on the strip to ensure proper deployment down to the water's surface (e.g., preventing the strip from being lifted and flapping due to wind) and proper spooling upon retrieval (e.g., slack in the line hinders smooth retrieval). The weight on the end of the strip is buoyant, so that it does not cause the strip to sink below the surface of the body of water. A metal guide-piece, such as guide member 506, is also in place below the spool to aid in proper spooling and to avoid snagging of the strip on the opening of the sampling container during retrieval. The guide member may have rounded edges to lessen scraping the hydrocarbons off of the sampling material during retrieval. The guide member may also be configured from two rollers. The guide member also prevents twisting during spooling. The buoyant weight 508 may be configured to not pass through the guide member to provide a stopping mechanism for the spooling mechanism.

As may be appreciated, the sampling container may involve different configurations. For example, the sampling container may be a rectangular prism to maximize the packing density of the containers and thus the quantity of samples onboard for a given space. The bottom surface may be a swinging door that is opened and closed using an electric motor that is housed outside of the sample container. Actuators may be disposed outside of the sample container to avoid contamination issues caused by lubricant oil, etc. The door may swing open using a hinge at one end of the sample container, such that the sample material may exit the sample container using gravity. The door orientation may be configured to prevent the door from interfering with the sample material as it is deployed and retrieved (e.g., positioned at the end of the sampling container that is near the front of the UV. When the door is opened, it should open as wide as possible, so as to avoid contacting or interfering with the sample material. The hinge should be configured to lessen it as a source of sample contamination, so the materials and lubrication should be carefully considered here. The door should make a tight seal when it is closed to isolate the sample material and oil sample from the environment. The doors may be firmly sealed even in extreme sea states where they are being rapidly accelerated and decelerated and being struck by waves. The seal may preferably be air and water tight. The door may also include a thermally insulating layer to reduce heat loss to the environment. The motor should be IP66 certified, which certifies that the device is dust tight and can prevent water ingress even while being washed down under high pressure. The rugged operating environment makes this necessary. The door and motor drive described are shown in FIGS. 6 and 7.

Figure 6:
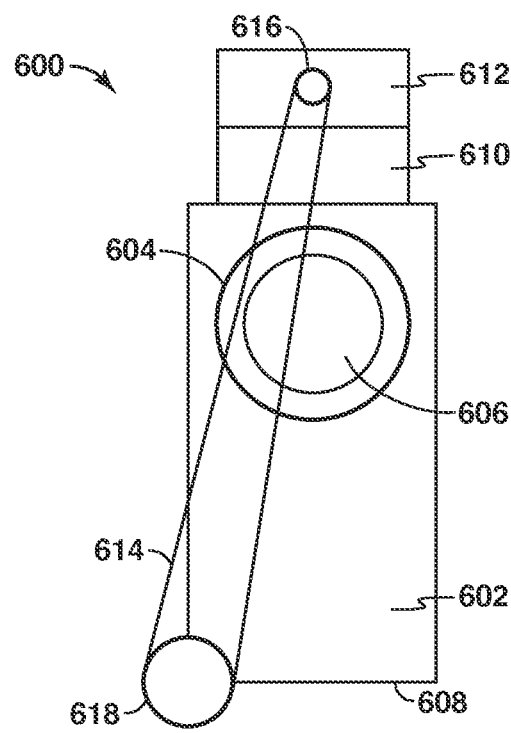
FIG. 6 is a diagram of an exemplary sample container having a motor drive in accordance with an exemplary embodiment of the present techniques.

FIG. 6 is a diagram of an exemplary sample container configuration 600 having a motor drive for the door in accordance with an exemplary embodiment of the present techniques. In this configuration 600, the sample container 602 may include a sampling material 604 may be disposed around a spool 606. Similar to the discussion of FIG. 5, the sampling material 604 may be attached to the spool 606 and use buoyant weight and guide member (not shown). In this configuration 600, a door 608 is disposed at the end of the sampling container adjacent to the body of water. The configuration 600 includes a first electric motor 610 that may be used to operate the spool 606 and a second electric motor 612 that is utilized to open and close the door 608. The first electric motor 610 is utilized to operate the spool 606 to deploy and retrieve the sampling material 604. The second electric motor 612 is utilized to open and close the door 608, which may utilize a belt or chain 614 and pulleys 616 and 618.

Figure 7:
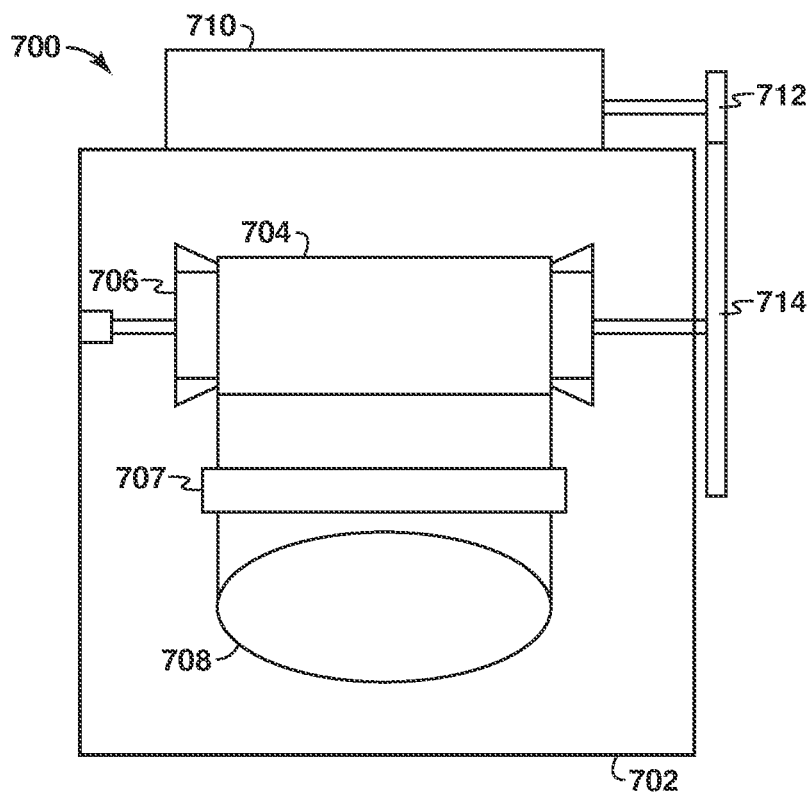
FIG. 7 is a diagram of an exemplary sample container configuration having a motor drive for the spool in accordance with an exemplary embodiment of the present techniques.

FIG. 7 is a diagram of an exemplary sample container configuration 700 having a motor drive 710 and a spool 706 in accordance with an exemplary embodiment of the present techniques. In this configuration 700, the sample container 702 may include a sampling material 704 that may be disposed around a spool 706. Similar to the discussion of FIGS. 5 and 6, the sampling material 704 may be attached to the spool 706 and use buoyant weight 707 and guide member 708. The electric motor 710 may be used to deploy and retrieve the sampling material 704 from the spool 706. The electric motor 710 is configured to engage with a shaft and a first gear 712, which is configured to engage with the second gear 714. The second gear 714 may be configured to engage with a shaft that coupled to the spool 706.

Through this coupling, the electric motor 710 deploys and retrieves the sampling material 704. The spool 706 may be rotated by the electric motor 710 to deploy and retrieve the sampling strip of sampling material 704. The actuator may be placed outside of the container to avoid contamination, and may be placed on top of the sampling container 702 to reduce the footprint of the sample container 702. The rotational motion may be transmitted to the spool axle via gears 712 and 714 on the outside of the sample container 702. The electric motor 710 and gears 712 and 714 may or may not need to have additional housing around them. The other end of the spool axle may be seated in a bearing hole to provide free rotation, while holding the axle in place. The motor 710 may be dust tight and can prevent water ingress even while being washed down under high pressure (e.g., IP66 certified). In this configuration 700, the sample container's opening through which the spool axle extends may also be sealed. That is, it should be an airtight and watertight seal to avoid any contamination. Additionally, the sealing material 704 may be considered as it could be a source of sample contamination. While it may be preferred to not use any lubrication for the spool axle (as shown in FIG. 7), it should be configured to lessen any sample contamination from the lubrication.

To enhance the operations, the spool may be configured to easily install and remove from the sample container. That is, the sample containers may be configured to provide easy removal and insertion for shipment to the lab. Accordingly, the configuration may include a design that provides a spool gear that is easy to remove (e.g., with a pin or nut securing the gear into the system). After the gear is removed, then the spool axle may be pulled out of the sample container, which results in the spool being free to drop out of the sampling container. A new spool may then installed by placing it into the container, sliding the axle, which may be keyed, through the spool, and securing the gear back on to lock the spool in place. As an example, the sampling container may be approximately 16 cm in width, 4 cm in depth, and 11 cm in height with an additional 5 cm of height below the container to accommodate the swinging door.

Figure 8:
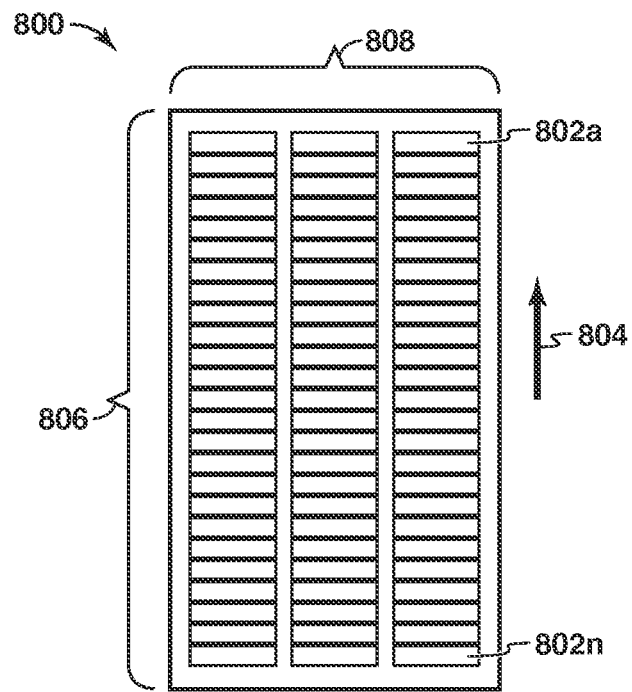
FIG. 8 is a diagram of an exemplary sample assembly having multiple sample containers in accordance with an exemplary embodiment of the present techniques.

The sample containers may be arranged into different configurations. For example, the sampling containers may be arranged and mounted within the sampling assembly, as shown below in FIG. 8. FIG. 8 is a diagram of an exemplary sample assembly 800 having multiple sample containers 802*a* to 802*n* in accordance with an exemplary embodiment of the present techniques. In this configuration 800, the sample assembly may be a rectangular prism that includes from 50 to 100 sampling containers 802*a* to 802*n*, which are also rectangular prisms. The sampling assembly may have a height 806, a width 808 and depth (not shown), which provide the dimensions of the rectangular prism. As an example, the sampling assembly 800 may be approximately 0.6 meters (m) in width, 11 cm in depth, and 1 m in height. This sampling assembly of such dimensions may include 75 sampling devices. The diagram is a view of the doors for the sampling containers 802*a*-802*n*, which may have one or more electric motors to open and close the doors and deploy and retrieve the sampling material from within the individual sampling containers 802*a*-802*n*. The sampling assembly may include additional space above for the motor and other components (e.g., which may be housed inside an enclosure) and have an additional space of about 5 cm of height below the container to accommodate the swinging door for the sampling containers 802*a*-802*n*.

The actual size of the sampling assembly depends largely upon the UV platform. In the sampling assembly, a gap around each sampling container (e.g., between 2 cm to 4 cm or about 3 cm) except where the containers are adjacent and connected to each other in the fore-aft direction. The fore and aft walls of the sample containers may be a shared piece of metal plate. The 3 cm gap may be utilized to accommodate the gear and belt drives on either side of the sampling containers and also to provide mechanism to flow a cooling fluid between the sampling containers. The temperature control components are explained further below.

Figure 9:
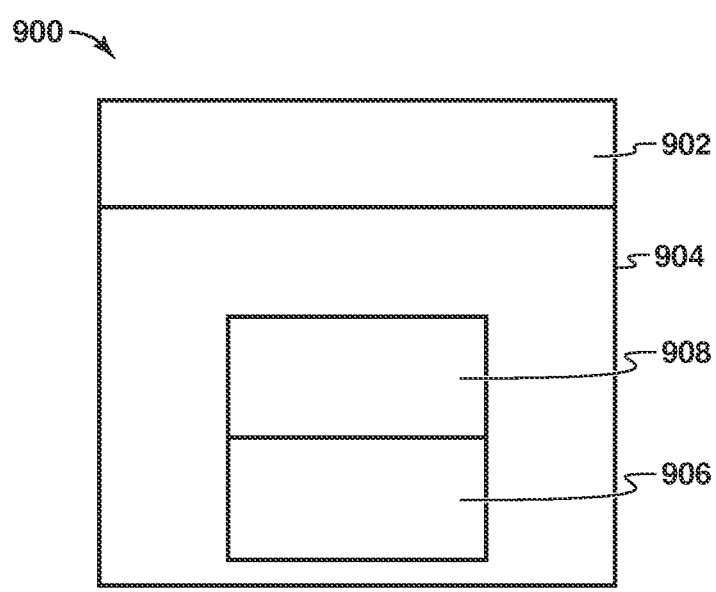
FIG. 9 is a diagram of an exemplary unmanned vehicle in accordance with an exemplary embodiment of the present techniques.

To collect samples, the sampling assembly may be disposed on an unmanned vehicle, as shown in FIG. 9. FIG. 9 is a diagram of an exemplary unmanned vehicle 900 in accordance with an exemplary embodiment of the present techniques. In this diagram, the sampling assembly 906 is disposed on an unmanned vehicle 904, which includes various components 902, which may be utilized for communication, sampling, hydrocarbon detection and/or identification, power distribution and/or propulsion along with managing autonomous operations, if necessary. The sampling assembly 906 may include various individual sample containers that are used to deploy the sampling material onto the surface of the body of water. The sampling material, which may be a strip, is sized so that approximately 1 m of the sampling material is in contact with the water's surface during sampling. The strip is then dragged through the waterborne liquid hydrocarbons based on the sampling pattern before being retrieved back into the sampling container, which is subsequently sealed shut.

Further still, the materials of construction of the UV and sampling assembly are evaluated to consider any possible contamination effects they may have on the obtained samples. Adequate freeboard may be preferred, so that the sampling material is not lifted by waves into the bottom surface of the sampling assembly during sampling operations. The configuration of the UV may be such that sampling may occur without the sampling material coming in contact with any part of the vessel.

Further, the unmanned vehicle 900 may also include heating and cooling components 908 to maintain the temperature of the samples within a specified range. For example, the sample temperatures may be maintained above $-10°$ C. to prevent irreversible crystallization of waxes. Further, if the sample temperatures are too high, bacteria may degrade the sample. Accordingly, heating and cooling components 908 may maintain the samples at temperatures between about $-10°$ C. and $10°$ C., temperatures between about $-5°$ C. and $10°$ C., and/or temperatures between about $4°$ C. and $5°$ C., which may be specified in ASTM D4489-95.

The cooling and heating components 908 may include various modules to operate. For example, the cooling and heating components 908 may include a mobile temperature management unit that maintains a heat transfer fluid. Exemplary mobile temperature management units are commercially available and utilized for the transport and temperature control of biological samples. In this configuration, the heat transfer fluid should be configured to not freeze or vaporize in expected temperatures that the UV may be exposed to during operations. The heat transfer fluid should also be compatible with the materials with which it is in contact. The temperature of the heat transfer fluid is controlled inside of the mobile temperature management unit, and it is circulated inside of the sampling assembly to heat or cool the sample containers, keeping their temperatures in the acceptable range.

Figure 10:
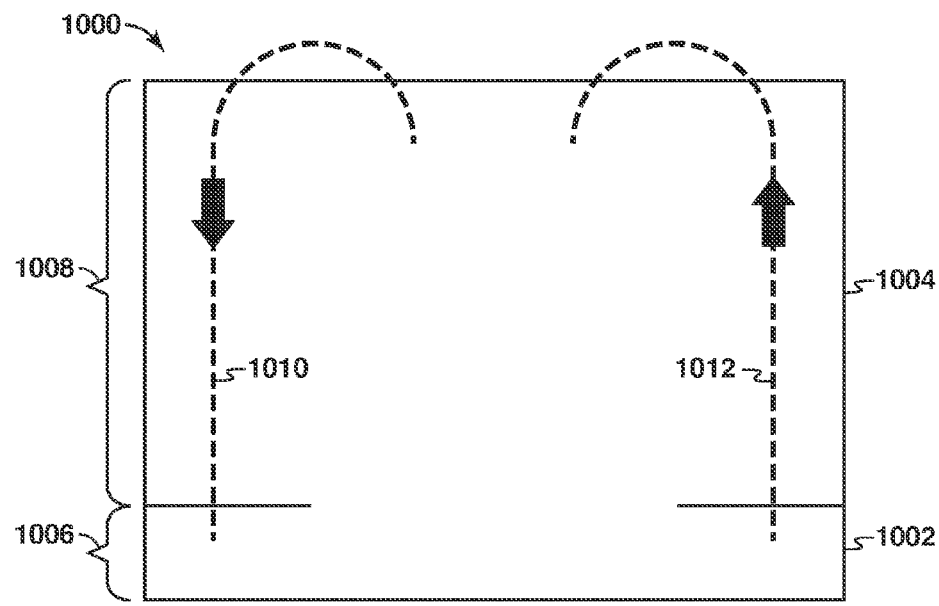
FIG. 10 is a diagram of an exemplary sample assembly and cooling and heating component in accordance with an exemplary embodiment of the present techniques.

As an example, FIG. 10 is a diagram 1000 of an exemplary sample assembly 1002 and cooling and heating component 1004 in accordance with an exemplary embodiment of the present techniques. In this diagram 1000, the sampling assembly 1002 is disposed below (e.g., closer to the body of water than) the cooling and heating component 1004. The cooling and heating component 1004 may include various conduits, temperature control sensors, heat transfer fluid and pumps that are utilized to maintain the sample containers within the sample assembly 1002 within a predetermined temperature range. As an example, the sampling assembly 1002 may have a depth 1006 of 0.15 m, while the cooling and heating component 1004 may have a depth of 0.6 m. The length and width may vary, but may be similar to the sampling assembly. As noted above for the sampling assembly example, the cooling and heating component 1004 may have a length that is 1 m and the width is 0.6 m, which may be disposed over the sampling assembly.

To maintain the temperature, the heat transfer fluid may be circulated, as shown by arrows 1010 and 1012, using a small pump located inside of the cooling and heating component 1004 or elsewhere. For cold environments, the heat transfer fluid may be a water-based fluid combined with an anti-freeze agent to prevent ice from forming. For warmer environments, the heat transfer fluid may include water and/or seawater. Other fluids and additives are also considered and combined with the heat transfer fluid, as may be appreciated. The heat transfer fluid does not have to completely fill the areas of the sampling assembly outside of the individual sampling containers. That is, an air gap may be provided in the top portion of the sampling assembly, so that any electric motors are not submerged. Further, the sampling assembly may be compartmentalized to help contain the heat transfer fluid below a certain level to reduce the amount of contact with the electric motors.

To manage the temperature, one or more thermocouples may be disposed in each sample container or adjacent to the sample containers to monitor the sample temperatures. This information may be stored (e.g., logged) and/or communicated to a control unit that may adjust the temperature by changing setting in the cooling and heating component 1004.

To provide quality assurance, a camera may be utilized to capture different aspects about the operations. That is, the camera may record interesting time segments of sampling operations in video or snapshot form. The camera may specifically record the deployment and/or sampling operations for each sample.

In one or more configurations, the samples may be processed on the UV via measurement components. Alternatively, the samples may be transported to another location for analysis. The analyses may include chemical and isotopic analysis (e.g. mass spectrometry and/or fluorometry and/or analysis for noble gases and isotopologues), sediment analysis, biological analysis (e.g. DNA analysis), and/or other methods. See, e.g., Chase, C. R., Lyra, G., & Green, M. (2010, October). Real-Time Monitoring of Oil Using Ultraviolet Filter Fluorometry. Sea Technology.

In one or more embodiments, the UV may be an unmanned surface vehicle and/or an unmanned airborne vehicle. If the UV is an unmanned surface vehicle, it may be a catamaran-style USV that is less than 7 m long and travels at speeds less than 7 kn. The USV may be transported in a standard 20 foot container from a deployment vessel. It may be deployed from a variety of vessels of opportunity or from the shore locations. A transit speed of around 3½ kn may be sufficient for some applications, while faster travel may be preferred to reduce the time between satellite acquisition and reaching a target location or attaining sufficient coverage of the target location.

The UV may be configured to perform the search and sampling patterns described in the previous paragraphs in an automated manner and/or via remote operations. For example, the UV may be deployed from a vessel performing other operations (e.g., seismic survey). Then, the UV may be launched into the body of water when target waterborne liquid hydrocarbons are identified. The operations of the UV may be controlled from the vessel by an operator. After deployment, the UV is controlled from the vessel from which it was launched or from another shore-based location. The UV is then retrieved from the body of water by the same vessel from which it was deployed or from shore or another vessel.

Data from the sensors onboard the UV may be communicated back to operators via communication equipment (e.g., Iridium satellite) and stored and analyzed in a database, while the UV is deployed. Commands may be sent to the UV from the shore or from a manned vessel. While the communications may be based on a variety of technologies, the UV may use an Iridium satellite link to provide the primary means for communicating navigation and sensor measurements to the remote operator. The same system may also be used as the primary means of relaying commands to the vehicle. When higher bandwidth is required, perhaps during sampling activities, the RUDICS satellite communication system may be used.

In additional embodiments, the UV is also equipped with additional sensors to further verify hydrocarbon seeps. For example, the sensors include a UV-flourometer(s) to screen the potential waterborne liquid hydrocarbons for possible anthropogenic contamination (e.g., diesel fuel) or other substances that indicate that the waterborne liquid hydrocarbons are not the result of a seep (e.g., meaning it is not of interest as it does not indicate the presence of a natural seep). Further, the detection of thermogenic hydrocarbons emanating from seafloor seeps, either at macro- or microscale is utilized to detect or confirm whether hydrocarbon seeps are present at these locations. Measuring concentrations of thermogenic methane, ethane, propane, butane, etc., is performed via compact high-sensitivity mass spectrometers and laser flourometer (for aromatic compounds generally associated with hydrocarbon liquids), which may be utilized onboard or deployed from the UV.

Additionally, these sensors within an UV can be used to map chemical or physical anomalies around waterborne liquid hydrocarbons to locate the potential seep vents or discharge locations. The analysis of the waterborne liquid hydrocarbons may provide information based on biological and chemical sampling of fluids, gases, and sediments. In particular, this method may include determining the presence of a potential seep or another source for the slick and estimating information, such as depth, type, quality, volume and location, about a subsurface hydrocarbon accumulation from the data from the sample. As an example, the present techniques involve the use of three independent technologies: clumped isotope geochemistry, noble gas geochemistry, and microbiology, which are combined and integrated as a workflow to enhance hydrocarbon exploration success. These three methods may provide information about the depth, fluid type (oil vs. gas) and quality, and volume of subsurface hydrocarbon accumulations to be determined from the sampling and analysis of hydrocarbon seeps (e.g., offshore and/or onshore). That is, the method may integrate existing and new biological and geochemical indicators to provide insights in opportunity identification. In addition, the integration of these biological and geochemical indicators with geological/geophysical contextual knowledge should further provide enhancements to hydrocarbon opportunity identification. These other techniques are described in Intl. Patent Application Pub. Nos. 2013119350; 2013148442; and 201307030, which are each incorporated herein in its entirety. Accordingly, in some embodiments, the present techniques may include performing one or more of microbial genomics; noble gas geochemistry and clumped isotope geochemistry of hydrocarbon phases from the sample. These techniques may be utilized to determine and/or estimate the presence and information, such as volume, depth, type, quality, and location of the subsurface hydrocarbon accumulation.

In one or more embodiments, the unmanned vehicle may include other components to perform the operations. For example, the UV may include a housing that encloses one or more of a communication component and associated antenna, a sample measurement component, another measurement component, a power component and a propulsion component. The modules and components may be provided power from the power component via power distribution lines (not shown). Similarly, the different modules and components may communicate with each other via communication lines. The central power and communication lines may be enclosed to be isolated from the environment and to manage the operation in an efficient manner.

To operate, the power component may be utilized to supply power to the propulsion component. Further, the power component may provide power to the communication component and the other measurement components. The power component may include a battery, motor and/or solar powered equipment. The batteries may provide power via the power distribution lines, which may include one or more cables, as an example. The motor may turn fuel into power, for example, by turning a generator, which may be used to power the modules and components and also to recharge the batteries.

The communication component may be utilized to exchange information between the different modules and components and/or the command unit via the communication lines and the communication antenna. The communication component may utilize the communication lines to handle the exchange of information, such as measured data, status indications or other notifications between the modules, such as the sample measurement component, the other measurement components, the power component and the propulsion component. The communication lines may include a bus, Ethernet cable, fiber optics or other suitable physical connection. In an alternative embodiment, the communication between modules may be via a wireless connection. Similarly, the communication protocol may be any protocol known to those skilled in the art. The communication components may include communication equipment that is utilized to communicate with one or more of other unmanned vehicles, marine vessels and/or command units. The communication equipment may utilize technologies, such as radio, cellular, wireless, microwave or satellite communication hardware and software.

To sample and measure the waterborne liquid hydrocarbons, the sample measurement component may be utilized to measure various features of the waterborne liquid hydrocarbons. Examples of different measurement components and the associated techniques to obtain measurements are noted further above.

The UV may include other features as well. For example, the UV may include an obstacle avoidance system to avoid other vessels, ice, and other hazards.

Figure 11:
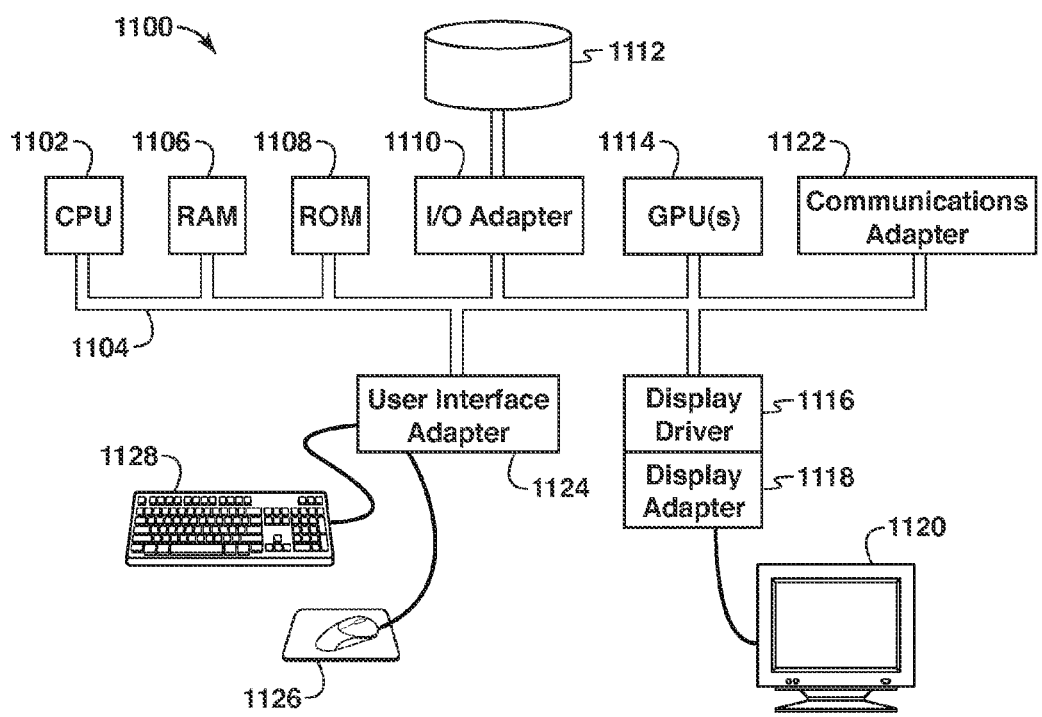
FIG. 11 is a block diagram of a computer system that may be used to perform any of the methods disclosed herein.

As an example, FIG. 11 is a block diagram of a computer system 1100 that may be used to perform any of the methods disclosed herein. A central processing unit (CPU) 1102 is coupled to system bus 1104. The CPU 1102 may be any general-purpose CPU, although other types of architectures of CPU 1102 (or other components of exemplary system 1100) may be used as long as CPU 1102 (and other components of system 1100) supports the inventive operations as described herein. The CPU 1102 may execute the various logical instructions according to disclosed aspects and methodologies. For example, the CPU 1102 may execute machine-level instructions for performing processing according to aspects and methodologies disclosed herein.

The computer system 1100 may also include computer components such as a random access memory (RAM) 1106, which may be SRAM, DRAM, SDRAM, or the like. The computer system 1100 may also include read-only memory (ROM) 1108, which may be PROM, EPROM, EEPROM, or the like. RAM 1106 and ROM 1108 hold user and system data and programs, as is known in the art. The computer system 1100 may also include an input/output (I/O) adapter 1110, a communications adapter 1122, a user interface adapter 1124, and a display adapter 1118. The I/O adapter 1110, the user interface adapter 1124, and/or communications adapter 1122 may, in certain aspects and techniques, enable a user to interact with computer system 1100 to input information.

The I/O adapter 1110 preferably connects a storage device(s) 1112, such as one or more of hard drive, compact disc (CD) drive, floppy disk drive, tape drive, etc. to computer system 1100. The storage device(s) may be used when RAM 1106 is insufficient for the memory requirements associated with storing data for operations of embodiments of the present techniques. The data storage of the computer system 1100 may be used for storing information and/or other data used or generated as disclosed herein. The communications adapter 1122 may couple the computer system 1100 to a network (not shown), which may enable information to be input to and/or output from system 1100 via the network (for example, a wide-area network, a local-area network, a wireless network, any combination of the foregoing). User interface adapter 1124 couples user input devices, such as a keyboard 1128, a pointing device 1126, and the like, to computer system 1100. The display adapter 1118 is driven by the CPU 1102 to control, through a display driver 1116, the display on a display device 1120. Information and/or representations of one or more 2D canvases and one or more 3D windows may be displayed, according to disclosed aspects and methodologies.

The architecture of system 1100 may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to the embodiments.

In one or more embodiments, the method may be implemented in machine-readable logic, such that a set of instructions or code that, when executed, performs automated sampling operations from memory. That is, the UV may be configured to operate in an autonomous mode. As an example, operating in an autonomous manner may include navigating and sampling the potential waterborne liquid hydrocarbons without the interaction of an operator. In such configurations, the UV may include a control unit, which may be the computer system 1100 as noted in FIG. 11. During the deployment, the unmanned vehicle may navigate toward targeted locations or may navigate along a specific search pattern. To navigate, the unmanned vehicle may utilize navigation components, which may include one or more propulsion components, one or more steering components and the like. The one or more propulsion components may include a motor coupled to one or more batteries and coupled to a propeller assembly, via a shaft, for example, as is known in the art. The propeller assembly may be utilized to move fluid in a manner to move the unmanned vehicle relative to the body of water. The navigation components may utilize sensors or other monitoring devices to obtain navigation data. The navigation data may include different types of navigational information, such as inertial motion unit (IMU), global positioning system information, compass information, depth sensor information, obstacle detection information, SONAR information, propeller speed information, seafloor map information, and/or other information associated with the navigation of the unmanned vehicle. The deployment may also include inserting certain equipment (e.g., certain monitoring components) into the unmanned vehicle for use in sampling operations. As an example, the deployment may include lowering the unmanned vehicle from the deck of a marine vessel into the body of water or dropping the unmanned vehicle into the body of water from an airborne vehicle.

The control unit may manage the operations of the communication components, sampling components, hydrocarbon detection and identification components, power components and propulsion components. The control unit may be configured to direct the navigation components to follow a direct trajectory to a target location and/or follow one or more search patterns. This may also involve adjusting operational parameters and/or settings to control the speed and direction. Further, the control unit may adjust the operation of the hydrocarbon detection and identification components. That is, the control unit may have the hydrocarbon detection and identification components perform the detection operations in a specific sequence. For example, the operations may involve deploying the balloon or a UAV with detection equipment to identify locations, then the flourometer and/or wavelength detection components may be utilized. This configuration may conserve power by having the long range detection components utilized initially, while the other short range components are utilized to verify the hydrocarbon location.

Further, the control unit may also control the sampling operations. As noted above, the sampling operations may be controlled by the control unit to obtain a certain number of samples, the duration the samples are in contact with the hydrocarbons on the body of water and other such operational aspects.

Illustrative, non-exclusive examples of systems and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

A method for identifying hydrocarbons comprising: obtaining a potential location of waterborne liquid hydrocarbons in a body of water using remote sensing data; directing an unmanned vehicle to the potential location; and obtaining a sample of the waterborne liquid hydrocarbons with the unmanned vehicle.

The method, further comprising: performing remote sensing in a survey area to identify the potential location of waterborne liquid hydrocarbons.

The method, wherein the remote sensing technology is synthetic aperture radar (SAR).

A method for identifying hydrocarbons comprising: transporting one or more sample containers on an unmanned vehicle to a potential location of waterborne liquid hydrocarbons in a body of water; contacting sampling material from one of the one or more sample containers with the waterborne liquid hydrocarbons; retrieving the sampling material having adhered waterborne liquid hydrocarbons as an obtained sample into one of the one or more sample containers on the unmanned vehicle; and storing the obtained sample in the sample container.

The method, wherein storing the sample comprises managing the temperature within the one of the one or more sample containers on the unmanned vehicle.

The method, wherein the temperature is maintained with the range between about $-10°$ C. and about $10°$ C.

The method, wherein obtaining the sample from the potential waterborne liquid hydrocarbons comprises removing live microbes from the obtained samples prior to determining whether the obtained samples is associated with a hydrocarbon system.

The method, wherein the unmanned vehicle is an unmanned surface vehicle (USV).

The method, wherein the unmanned vehicle is an unmanned airborne vehicle (UAV).

The method, further comprising: determining whether the obtained sample is associated with a hydrocarbon system.

The method, further comprising: using the determination to perform hydrocarbon exploration operations.

The method, further comprising searching for waterborne liquid hydrocarbons in the body of water from the potential location.

The method, wherein searching for waterborne liquid hydrocarbons comprises: performing a large pattern search from the potential location, wherein the large pattern search comprises detecting hydrocarbons; if hydrocarbons are detected, performing a sampling pattern search to obtain the sample; and if hydrocarbons are not detected, determining whether to continue the large pattern search.

The method, wherein searching for waterborne liquid hydrocarbons comprises pumping surface compounds through a flourometer to identify hydrocarbons.

The method, wherein searching for waterborne liquid hydrocarbons comprises analyzing the surface of the body of water to detect certain wavelengths to identify hydrocarbons.

The method, wherein searching for waterborne liquid hydrocarbons comprises: deploying a balloon above the unmanned vehicle; obtaining infrared and visible light images; and analyzing the infrared and visible light images to identify hydrocarbons.

The method, wherein searching for waterborne liquid hydrocarbons comprises: deploying a unmanned aerial vehicle above the unmanned vehicle; obtaining infrared and visible light images with the unmanned aerial vehicle; and analyzing the infrared and visible light images to identify hydrocarbons.

The method, wherein searching for waterborne liquid hydrocarbons comprises: deploying a unmanned aerial vehicle above the unmanned vehicle; generating an ultraviolet light; obtaining images with the unmanned aerial vehicle; and analyzing the ultraviolet images to identify hydrocarbons.

The method, further comprising obtaining one or more images as the sample is being obtained.

The method, further comprising: transporting one or more sample containers on a deployment unmanned vehicle to a potential location of waterborne liquid hydrocarbons in a body of water; contacting sampling material from one of the one or more sample containers with the waterborne liquid hydrocarbons; retrieving the sampling material having adhered waterborne liquid hydrocarbons as an obtained sample into one of the one or more sample containers on the unmanned vehicle; and storing the obtained sample in the sample container on the unmanned vehicle.

The method, wherein each of the one or more sample containers comprises the sampling material disposed within the sample container.

The method, wherein each of the one or more sample containers is configured to: seal the sampling material within the sample container if hydrocarbons are not detected; unseal the sample container to provide interaction between the sampling material and the waterborne liquid hydrocarbons in a body of water when hydrocarbons are detected.

The method, wherein the sample container is configured to seal the sample container after a set period of time once the sample container has been unsealed.

The method, wherein the deployment unmanned vehicle is an unmanned airborne vehicle.

The method, wherein the unmanned vehicle is an unmanned surface vehicle.

The method, wherein the unmanned vehicle is configured to collect the one of the one or more sample containers via a magnet.

The method, wherein storing the obtained sample comprises managing the temperature within the one of the one or more sample containers on the unmanned vehicle.

The method, wherein the temperature is maintained with the range between about −10° C. and about 10° C.

A hydrocarbon identification system comprising: an unmanned vehicle having a propulsion component, a communication component and a sample measurement component, wherein the propulsion component is configured to maneuver the unmanned vehicle, the sample measurement component is configured to obtain one or more samples for the waterborne liquid hydrocarbons and the communication component is configured to communicate signals associated with the obtained samples.

The system, wherein the unmanned vehicle is configured to be controlled via remote control communications.

The system, wherein the unmanned vehicle is configured to be autonomously operated.

The system, wherein the sample measurement component comprises a sample assembly having a plurality of individual sampling containers.

The system, wherein each of the sampling containers has a sampling material disposed around a spool within the sampling container.

The system, wherein each of the sampling containers has buoyant weight coupled to the sampling material.

The system, wherein each of the sampling containers has a guide member disposed between the spool and the buoyant weight.

The system, wherein the sample measurement component comprises a sampling electric motor configured to lower the sampling material into the open and close a door for one or more of the sampling containers.

The system, wherein the sample measurement component comprises a door electric motor configured to open and close a door for one or more of the sampling containers.

The system, wherein the sampling assembly has between 50 and 100 sampling containers.

The system, wherein the sampling material is TFE-fluorocarbon polymer screening fabric.

The system, wherein the unmanned vehicle has a heating and cooling component configured to maintain the temperature within each of the sampling containers within a specified range.

The system, wherein the unmanned vehicle is an unmanned surface vehicle (USV).

The system, wherein the unmanned vehicle is an unmanned airborne vehicle (UAV).

The system, wherein the unmanned vehicle has a control unit configured to communicate with the propulsion component to perform a large pattern search to detect hydrocarbons in an automated manner.

The system, wherein the unmanned vehicle has a control unit configured to communicate with the propulsion component to perform a large pattern search to detect hydrocarbons in an automated manner.

The system, wherein the unmanned vehicle has a hydrocarbon detection component configured to identify hydrocarbons.

The system, wherein the hydrocarbon detection component comprises a flourometer and a pump, wherein the pump is configured to obtain surface compounds and pass the surface compounds to the flourometer to identify hydrocarbons.

The system, wherein the hydrocarbon detection component comprises a receiver configured to receive images from the surface of the body of water; and analyze the images to identify certain wavelengths associated with hydrocarbons.

The system, wherein the hydrocarbon detection component comprises a balloon having an infrared and visible camera and configured to: obtain infrared and visible light images from the surface of the body of water; and an analyzer configured to determine hydrocarbons from the infrared and visible light images.

The system, wherein the unmanned vehicle has a camera configured to obtain one or more images as one or more samples are obtained.

The system, further comprising a deployment unmanned vehicle having a deployment propulsion component, a deployment communication component, a sample deployment component and a deployment measurement component, wherein the deployment propulsion component is configured to maneuver the deployment unmanned vehicle, the deployment measurement component is configured to identify waterborne liquid hydrocarbons, the sample deployment component is configured to deploy a sample container into the identified waterborne liquid hydrocarbons, and the deployment communication component is configured to communicate signals associated with the operation of the deployment unmanned vehicle.

The system, wherein the sample container comprise a canister having the sampling material disposed within the canister.

The system, wherein the sample measurement component is configured to retrieve the sample container.

The system, wherein the unmanned vehicle has a heating and cooling component configured to maintain the temperature within the sampling container within a specified range.

The system, wherein the sample container is configured to: seal the sampling material within the sample container if hydrocarbons are not detected; unseal the sample container to provide interaction between the sampling material and the waterborne liquid hydrocarbons in a body of water when hydrocarbons are detected.

The system, wherein the sample container is configured to seal the sample material within the sample container after a set period of time once the sample container has been unsealed.

The system, wherein the deployment unmanned vehicle is a deployment unmanned airborne vehicle.

The system, wherein the unmanned vehicle is an unmanned surface vehicle.

The system, wherein the unmanned vehicle is configured to collect the sample container via a magnet.

It should be understood that the preceding is merely a detailed description of specific embodiments of the invention and that numerous changes, modifications, and alternatives to the disclosed embodiments can be made in accordance with the disclosure here without departing from the scope of the invention. The preceding description, therefore, is not meant to limit the scope of the invention. Rather, the scope of the invention is to be determined only by the appended claims and their equivalents. It is also contemplated that structures and features embodied in the present examples can be altered, rearranged, substituted, deleted, duplicated, combined, or added to each other. The articles "the", "a" and "an" are not necessarily limited to mean only one, but rather are inclusive and open ended so as to include, optionally, multiple such elements.

The invention claimed is:

1. A method for identifying hydrocarbons comprising:
   transporting a sampling assembly comprising a plurality of individual sample containers on an unmanned vehicle to a potential location of waterborne liquid hydrocarbons in a body of water, wherein the unmanned vehicle is an unmanned surface vehicle (USV) and wherein each of the sample containers has a sampling material disposed around a spool within the sampling container;
   dispensing the sampling material from the spool of one or more of the sample containers and contacting the sampling material with the waterborne liquid hydrocarbons;
   retrieving the sampling material having adhered waterborne liquid hydrocarbons as an obtained sample into the one or more sample containers on the unmanned vehicle;
   storing the obtained sample in the sample container; and
   maintaining the temperature within one or more of the sampling containers in the sampling assembly in the range of between about −10° C. and about 10° C.

2. The method of claim 1, wherein the temperature is maintained within the range between about −5° C. and about 10° C.

3. The method of claim 1, further comprising removing live microbes from the obtained samples prior to determining whether the obtained samples is associated with a hydrocarbon system.

4. The method of claim 1, further comprising searching for waterborne liquid hydrocarbons in the body of water from the potential location.

5. The method of claim 4, wherein searching for waterborne liquid hydrocarbons comprises:
   performing a large pattern search from the potential location, wherein the large pattern search comprises detecting hydrocarbons;
   if hydrocarbons are detected, performing a sampling pattern search to obtain the sample; and
   if hydrocarbons are not detected, determining whether to continue the large pattern search.

6. The method of claim 4, wherein searching for waterborne liquid hydrocarbons comprises analyzing the surface of the body of water to detect certain wavelengths to identify hydrocarbons.

7. The method of claim 4, wherein searching for waterborne liquid hydrocarbons comprises:
   deploying a balloon above the unmanned vehicle, wherein the balloon comprises infrared and visible light detection components;
   obtaining infrared and visible light images; and
   analyzing the infrared and visible light images to identify hydrocarbons.

8. The method of claim 4, wherein searching for waterborne liquid hydrocarbons comprises:
   deploying an unmanned aerial vehicle above the unmanned vehicle, wherein the unmanned aerial vehicle comprises visible and infrared light cameras;
   obtaining infrared and visible light images with the unmanned aerial vehicle; and
   analyzing the infrared and visible light images to identify hydrocarbons.

9. The method of claim 4, wherein searching for waterborne liquid hydrocarbons comprises:
   deploying a unmarried aerial vehicle above the unmanned vehicle;
   generating an ultraviolet light;
   obtaining images with the unmanned aerial vehicle; and
   analyzing the ultraviolet images to identify hydrocarbons.

10. A hydrocarbon identification system comprising:
    an unmanned vehicle having a propulsion component, a communication component, and a sample measurement component, wherein the propulsion component is configured to maneuver the unmanned vehicle, the sample measurement component is configured to obtain one or more samples of a waterborne liquid hydrocarbons, and the communication component is configured to communicate signals associated with the obtained samples;
    wherein the unmanned vehicle is an unmanned surface vehicle (USV);
    wherein the sample measurement component comprises a sample assembly having a plurality of individual sampling containers and wherein each of the sampling containers has a sampling material disposed around a spool within the sampling container; and
    wherein the unmanned vehicle has a heating and cooling component configured to maintain the temperature within each of the sampling containers within the range of between about −10° C. and about 10° C.

11. The system of claim 10, wherein the unmanned vehicle is configured to be controlled via a remote control communications.

12. The system of claim 10, wherein the unmanned vehicle is configured to be autonomously operated.

13. The system of claim 10, wherein each of the sampling containers has buoyant weight coupled to the sampling material.

14. The system of claim 13, wherein each of the sampling containers has a guide member disposed between the spool and buoyant weight.

15. The system of claim 10, wherein the sampling assembly has between 50 and 100 sampling containers.

16. The system of claim 10, wherein the sampling material is TFE-fluorocarbon polymer screening fabric.

17. The system of claim 10, wherein the unmanned vehicle has a hydrocarbon detection component configured to identify hydrocarbons.

18. The system of claim 17, wherein the hydrocarbon detection component comprises a receiver configured to receive images from the surface of the body of water, and analyze the images to identify certain wavelengths associated with hydrocarbons.

19. The system of claim 17, wherein the hydrocarbon detection component comprises a balloon having an infrared and visible camera and configured to:
  obtain infrared and visible light images from the surface of the body of water; and
  an analyzer configured to determine hydrocarbons from the infrared and visible light images.

20. The system of claim 10, further comprising a deployment unmanned vehicle having a deployment propulsion component, a deployment communication component, a sample deployment component, and a deployment measurement component, wherein the deployment propulsion component is configured to maneuver the deployment unmanned vehicle, the deployment measurement component is configured to identify waterborne liquid hydrocarbons, the sample deployment component is configured to deploy a sample container into the identified waterborne liquid hydrocarbons, and the deployment communication component is configured to communicate signals associated with the operation of the deployment unmanned vehicle.

* * * * *